US009402855B2

(12) United States Patent
Bishop et al.

(10) Patent No.: US 9,402,855 B2
(45) Date of Patent: Aug. 2, 2016

(54) METHOD OF TREATING AND PREVENTING SECONDARY HYPERPARATHYROIDISM

(71) Applicants: CYTOCHROMA INC., Markham (CA); PROVENTIV THERAPEUTICS, LLC, Bannockburn, IL (US)

(72) Inventors: Charles W. Bishop, Mount Horeb, WI (US); Keith H. Crawford, Highlands Ranch, CO (US); Eric J. Messner, Lake Forest, IL (US); P. Martin Petkovich, Kingston (CA); Christian F. Helvig, Markham (CA)

(73) Assignees: OPKO RENAL, LLC, Miami, FL (US); OPKO IRELAND GLOBAL HOLDINGS, LTD., Grand Cayman (KY)

( * ) Notice: Subject to any disclaimer, the term of this patent is extended or adjusted under 35 U.S.C. 154(b) by 519 days.

(21) Appl. No.: 13/680,997

(22) Filed: Nov. 19, 2012

(65) Prior Publication Data
US 2013/0178451 A1 Jul. 11, 2013

Related U.S. Application Data

(63) Continuation of application No. 12/305,572, filed as application No. PCT/US2007/071791 on Jun. 21, 2007, now Pat. No. 8,329,677.

(60) Provisional application No. 60/815,148, filed on Jun. 21, 2006.

(51) Int. Cl.
*A61K 31/59* (2006.01)
*A61K 31/593* (2006.01)
*A61K 31/592* (2006.01)

(52) U.S. Cl.
CPC .............. *A61K 31/593* (2013.01); *A61K 31/59* (2013.01); *A61K 31/592* (2013.01)

(58) Field of Classification Search
CPC .... A61K 31/59; A61K 31/592; A61K 31/593
USPC .......................................................... 514/167
See application file for complete search history.

(56) References Cited

U.S. PATENT DOCUMENTS

| 3,565,924 A | 2/1971 | DeLuca et al. |
| 3,880,894 A | 4/1975 | De Luca et al. |
| 4,004,003 A | 1/1977 | Babcock et al. |
| 4,230,701 A | 10/1980 | Holick et al. |
| 4,335,120 A | 6/1982 | Holick et al. |
| 4,442,093 A | 4/1984 | Maeda et al. |
| 4,555,364 A | 11/1985 | DeLuca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |
| 4,729,895 A | 3/1988 | Makino et al. |
| 4,755,544 A | 7/1988 | Makino et al. |
| 4,997,824 A | 3/1991 | Popovtzer et al. |
| 5,026,559 A | 6/1991 | Eichel et al. |
| 5,160,742 A | 11/1992 | Mazer et al. |
| 5,328,903 A | 7/1994 | Ishii et al. |
| 5,403,831 A | 4/1995 | DeLuca et al. |
| 5,487,900 A | 1/1996 | Itoh et al. |
| 5,529,991 A | 6/1996 | Knutson et al. |

(Continued)

FOREIGN PATENT DOCUMENTS

| CA | 2241205 A1 | 7/1997 |
| EP | 0 227 836 A1 | 7/1987 |

(Continued)

OTHER PUBLICATIONS

"K/DOQI Clinical Practice Guidelines for Bone Metabolism and Disease in Chronic Kidney Disease," National Kidney Foundation, *Am. J. Kidney Dis.*, 42 (Supplement 3):1-202 (2003).
Al-Aly, Z., "Changes in Serum 25-Hydroxyvitamin D and Plasma Intact PTH Levels Following Treatment with Ergocalciferol in Patients With CKD," Am. J. Kid. Dis., 50(1):59-68 (2007).
Amin, "The impact of improved phosphorus control: use of sevelamer hydrochloride in patients with chronic renal failure," *Nephrol Dial Transplant*, 17:340-345 (2002).
Andress, "Vitamin D in chronic kidney disease: A systematic role for selective vitamin D receptor activation," *Kidney Int.*, 69:33-43 (2006).
Arekat et al., "Dramatic Improvement of BMD Following Vitamin D Therapy in a Bone Marrow Transplant Recipient," *J. Clin. Densitometry*, 5:267-271 (2002).

(Continued)

*Primary Examiner* — San-Ming Hui
(74) *Attorney, Agent, or Firm* — Marshall, Gerstein & Borun LLP

(57) ABSTRACT

The method of treating elevated blood levels of iPTH by increasing or maintaining blood concentrations of both 25-hydroxyvitamin D and 1,25-dihydroxyvitamin D in a patient by administering, as necessary, both Vitamin D repletion and Vitamin D hormone replacement therapies, is disclosed. The blood concentrations of 25-hydroxyvitamin D are increased to and maintained at or above 30 ng/mL, and blood concentrations of 1,25-dihydroxyvitamin D are increased to or maintained within a patient's normal historical physiological range for 1,25-dihydroxyvitamin D without causing substantially increased risk of hypercalcemia, hyperphosphatemia or over suppression of plasma iPTH in the patient. The blood levels of 25-hydroxyvitamin D are maintained at or above 30 ng/mL between doses of Vitamin D repletion therapies, and the blood levels of 1,25-dihydroxyvitamin D are maintained in the patient's normal historical physiological range between doses of Vitamin D hormone replacement therapies. In one aspect, the disclosure includes methods wherein the blood concentration of 25-hydroxyvitamin D during treatment comprises predominantly 25-hydroxyvitamin $D_3$, and/or wherein the method includes administering predominantly or solely 25-hydroxyvitamin $D_3$ for 25-hydroxyvitamin D repletion and/or maintenance.

21 Claims, No Drawings

(56) References Cited

U.S. PATENT DOCUMENTS

| | | | |
|---|---|---|---|
| 5,593,690 | A | 1/1997 | Akiyama et al. |
| 5,602,116 | A | 2/1997 | Knutson et al. |
| 5,614,513 | A | 3/1997 | Knutson et al. |
| 5,622,941 | A | 4/1997 | Knutson et al. |
| 5,693,615 | A | 12/1997 | Stone |
| 5,707,980 | A | 1/1998 | Knutson et al. |
| 5,795,882 | A | 8/1998 | Bishop et al. |
| 5,861,386 | A | 1/1999 | Knutson et al. |
| 5,869,473 | A | 2/1999 | Knutson et al. |
| 6,051,567 | A | 4/2000 | Abrahamson et al. |
| 6,133,250 | A | 10/2000 | Knutson et al. |
| 6,139,875 | A | 10/2000 | Adams et al. |
| 6,147,064 | A | 11/2000 | Knutson et al. |
| 6,150,346 | A | 11/2000 | Knutson et al. |
| 6,190,591 | B1 | 2/2001 | van Lengerich |
| 6,190,695 | B1 | 2/2001 | Hoshino et al. |
| 6,228,849 | B1 | 5/2001 | Thys-Jacobs |
| 6,265,392 | B1 | 7/2001 | Abrahamson et al. |
| 6,274,169 | B1 | 8/2001 | Abrahamson et al. |
| 6,342,249 | B1 | 1/2002 | Wong et al. |
| 6,376,479 | B1 | 4/2002 | Knutson et al. |
| 6,380,408 | B1 | 4/2002 | Posner et al. |
| 6,432,936 | B1 | 8/2002 | DeLuca et al. |
| 6,596,314 | B2 | 7/2003 | Wong et al. |
| 6,903,083 | B2 | 6/2005 | Knutson et al. |
| 6,923,988 | B2 | 8/2005 | Patel et al. |
| 6,929,803 | B2 | 8/2005 | Wong et al. |
| 6,982,258 | B2 | 1/2006 | Posner et al. |
| 7,101,865 | B2 | 9/2006 | Posner et al. |
| 2002/0183288 | A1 | 12/2002 | Mazess et al. |
| 2004/0043971 | A1 | 3/2004 | Mazess et al. |
| 2004/0101554 | A1 | 5/2004 | Kirschner et al. |
| 2005/0101576 | A1 | 5/2005 | Whitehouse et al. |
| 2005/0124591 | A1 | 6/2005 | Tian et al. |
| 2005/0148557 | A1 | 7/2005 | Tian et al. |
| 2006/0193877 | A1 | 8/2006 | Tengler et al. |
| 2009/0176748 | A1 | 7/2009 | Tabash et al. |
| 2009/0311316 | A1 | 12/2009 | Bishop et al. |

FOREIGN PATENT DOCUMENTS

| | | |
|---|---|---|
| EP | 0 508 756 A1 | 10/1992 |
| EP | 2037936 B1 | 6/2014 |
| JP | S55-139320 | 10/1980 |
| JP | S57-188520 A | 11/1982 |
| JP | S64-031722 A | 2/1989 |
| JP | 04-208225 A | 7/1992 |
| JP | 07-242550 A | 9/1995 |
| JP | 08-092098 A | 4/1996 |
| JP | 10-158171 A | 6/1998 |
| JP | H11-158074 A | 6/1999 |
| JP | 2004-175750 A | 6/2004 |
| WO | WO-91/16899 A1 | 11/1991 |
| WO | WO-94/00128 A1 | 1/1994 |
| WO | WO-96/00074 A1 | 1/1996 |
| WO | WO-96/31215 A1 | 10/1996 |
| WO | WO-97/11053 A1 | 3/1997 |
| WO | WO-91/12807 A1 | 9/1997 |
| WO | WO-98/18610 A1 | 5/1998 |
| WO | WO-99/11272 A1 | 3/1999 |
| WO | WO-00/21504 A1 | 4/2000 |
| WO | WO-00/35419 A2 | 6/2000 |
| WO | WO-03/039572 A1 | 5/2003 |
| WO | WO-03/047595 A1 | 5/2003 |
| WO | WO-03/047595 A1 | 6/2003 |
| WO | WO-2004/028515 A1 | 4/2004 |
| WO | WO-2004/058235 A2 | 7/2004 |
| WO | WO-2004/080467 A2 | 9/2004 |
| WO | WO-2005/011652 A2 | 2/2005 |
| WO | WO-2005/123120 A1 | 12/2005 |
| WO | WO-2007/047327 A2 | 4/2007 |
| WO | WO-2007/092755 A2 | 8/2007 |
| WO | WO-2008/008608 A2 | 1/2008 |
| WO | WO-2008/134523 A1 | 11/2008 |
| WO | WO-2010/011906 A1 | 1/2010 |

OTHER PUBLICATIONS

Armas et al., "Vitamin D2 is Much Less Effective than Vitamin D3 in Humans," *J. Clin. Endocrinol. Metab.*, 89:5387-5391 (2004).

Bagnis et al., "Biochemical and Hormonal Short-Term Effects of 25-hydroxyvitamin D3 in Patients on Continuous Peritoneal Dialysis," *Ital. J. Mineral Electrolyte Metab.*, 12:73-76 (1998).

Bailie et al. "Comparative Review of the Pharmacokinetics of Vitamin D Analogues," *Seminars in Dialysis*, 15(5):352-357 (2000).

Baird et al., "Steroid Dynamics Under Steady-State Conditions," *Recent Prog. Horm. Res.*, 25:611-664 (1969).

Barger-Lux M.J. et al., "Vitamin D and Its Major Metabolites: Serum Levels After Graded Oral Dosing in Healthy Men" *Osteoporosis International*, United Kingdom, 8(3):222-230 (1998).

Barreto et al., "25-Hydroxyvitamin D3, the Prohormone of 1,25-Dihydroxyvitamin D3, Inhibits the Proliferation of Primary Prostatic Epithelial Cells," *Cancer Epidemiol, Biomarkers & Prevention*, 9:265-270 (2000).

Beckman, et al., "Up-Regulation of the Intestinal 1, 25-Dihydroxyvitamin D Receptor During Hypervitaminosis D: A Comparison Between Vitamin D2 and Vitamin D31," Biochemical and Biophysical Research Communications, vol. 169, No. 3, pp. 910-915 (Jun. 29, 1990).

Beer et al., "Pharmacokinetics and Tolerability of a Single Dose of DN-101, a New Formulation of Calcitriol, in Patients with Cancer," *Clin. Cancer Res.*, 11:7794-7799 (2005).

Bell et al., "Evidence that 1,25-Dihydroxyvitamin D3 Inhibits the Hepatic Production of 25-Hydroxyvitamin D in Man," *J. Clin. Invest.*, 74:1540-1544 (1984).

Belostotsky et al., "A single high dose of ergocalciferol can be used to boost 25-hydroxyvitamin D levels in children with kidney disease," *Pediatr Nephrol*, 24:625-626 (2009).

Bianchi et al., "No Difference in Intestinal Strontium Absorption After an Oral or an Intravenous 1,25(OH)2D3 Bolus in Normal Subjects," *J. Bone Miner. Res.*, 14:1789-1795 (1999).

Blair et al., "Prevalence of vitamin D [25(OH)D] deficiency and effects of supplementation with ergocalciferol (vitamin D2) in stage 5 chronic kidney disease patients." *J.Ren Nutr.*, 18: 375-382 (2008).

Bordier et al., "Evolution of renal osteodystrophy: Correlation of bone histomorphometry and serum mineral and immunoreactive parathyroid hormone values before and after treatment with calcium carbonate or 25-hydroxycholecalciferol," *Kidney Int Suppl*, 2:S102-S112 (1975).

Bouillon et al., "Influence of dialysate calcium concentration and vitamin D on serum parathyroid hormone during repetitive dialysis," *Kidney Int.*, 7:422-432 (1975).

Briese et al., "Arterial and cardiac disease in young adults with childhood-onset end-stage renal disease-impact of calcium and vitamin D therapy," *Nephrology Dialysis Transplantation.*, 21:1906-1914 (2006).

Brossard et al. "Influence of Glomerular Filtration Rate on Non-(1-84) Parathyroid Hormone (PTH) Detected by Intact PTH Assays," *Clinical Chemistry*, 46(5):697-703 (2000).

Brown et al., "Vitamin D Analogues for Secondary Hyperparathyroidism," Nephrol Dial Transplant, 17[Suppl. 10]:10-19 (2002).

Buccianti et al., "Effects of Calcifediol Treatment on the Progression of Renal Osteodystrophy during Continuous Ambulatory Peritoneal Dialysis," *Nephron*, 56:353-356 (1990).

Budavari (ed.), *Merck Index: an Encyclopedia of Chemicals, Drugs, and Biologicals*, 11th Edition, Merck & Co., 9927-9930 (1989).

Bulla et al., "Renal bone disorders in children: therapy with vitamin D3 or 1,25-dihydroxycholecalciferol," *Proc.Eur.Dial.Transplant.Assoc.*, 16: 644-648 (1979).

Chandra et al., "Cholecalciferol (vitamin D3) therapy and vitamin D insufficiency in patients with chronic kidney disease: a randomized controlled pilot study," *Endocr.Pract.*, 14:10-17 (2008).

Claris-Appiani et al., "Phosphate-Induced PTH Stimulation and Calcitriol Treatment in Children with Early Chronic Renal Insufficiency," *J. Bone Miner. Met.*, 12:S91-S97 (1994).

(56) References Cited

OTHER PUBLICATIONS

Coburn, "An Update on Vitamin D as Related to Nephrology Practice: 2003," *Kidney International*, vol. 64, Supplement 87, pp. S125-S130 (2003).

Coburn, et al., "Use of Active Vitamin D Sterols in Patients with Chronic Kidney Disease, Stages 3 and 5," *Kidney International*, vol. 63, Supplement 85, pp. S49-S53 (2003).

Coen et al., "1,25(OH)2D3 and 25-OHD3 in the Treatment of Renal Osteodystrophy: Comparison of Combined Versus 1,25(OH)2D3 Administration Alone," *Miner. Electrolyte Metab.*, 9:19-27 (1983).

Coen et al., "25-hydroxycholecalciferol in the treatment of renal osteodystrophy in haemodialysed patients," *Int J Artificial Organs*, 2(6): 278-281 (1979).

Cohen-Solal et al., "Non-Aluminic Adynamic Bone Disease in Non-Dialyzed Uremic Patients: A New Type of Osteopathy Due to Overtreatment?" *Bone*, 13:1-5 (1992).

Collet et al. "Modified-Release Peroral Dosage Forms," Aulton (ed.), Pharmaceutics: The Science of Dosage Forms, Churchill Livingston, London, pp. 289-305 (2002).

Colodro et al., "Effect of 25-Hydroxy-Vitamin D3 on Intestinal Absorption of Calcium in Normal Man and Patients With Renal Failure," *Metabolism*, 27(6):745-753 (1978).

Cooke et al., "Vitamin D-Binding Protein (Gc-Globulin): Update 1995," *Endocrine Rev.*, 4:125-128 (1995).

Coyne et al., "Paricalcitol Capsule for the Treatment of Secondary Hyperparathyroidism in Stages 3 and 4 CKD," *American Journal of Kidney Diseases*, 47(2):263-276 (2006).

Daisley-Kydd et al., "Calcitriol in the Management of Secondary Hyperparathyroidism of Renal Failure," *Pharmacotherapy.*, 16:619-630 (1996).

Davies, M. et al. The Absorption and Metabolism of Vitamin D3 from Parenteral Injection Sites, Proceedings of the Workshop on Vitamin D, 4th, Vitam. D: Basic Res. Its Clin. Appl. (1979), abstract.

DB-Pharma, "Dedrogyl 15 Mg/10ML Calcifediol Oral Drops, Solution," Marketing Authorization No. 317 863.2 (2000).

DeLuca, "Treatment of renal osteodystrophy with 25-hydroxycholecalciferol," *Arch Intern Med*, 126(5):896-899 (1970).

Deroisy et al., "Comparison of the Short-Term Effects of Three Oral Calcium-Vitamin D Formulations and Placebo on Calcium Metabolism," *Curr. Ther. Res.*, 59:370-378 (1998).

DeVille et al., "Effect of Ergocalciferol Supplementation on Serum Parathyroid Hormone and Serum 25-Hydroxyvitamin D in Chronic Kidney Disease," *Nephrology*, 11:555-559 (2006).

*Dietary Reference Intakes for Calcium, Phosphorus, Magnesium, Vitamin D, and Fluoride*, Standing Committee on the Scientific Evaluation of Dietary Reference Intakes, Food and Nutrition Board, Institute of Medicine, National Academy Press, Washington DC, pp. 250-287 (1997).

*Dietary Supplement Fact Sheet: Vitamin D*, National Institutes of Health, Office of Dietary Supplements (last update: Aug. 5, 2005), retrieved from <URL: http:ods.od.nih.gov/factsheets/vitamind.asp> on Aug. 31, 2007.

*Disease and Vitamin D*, University of California Riverside, retrieved from Internet, <URL: <http://vitamind.ucr.edu/disease.html>> (last update: May 19, 1999).

Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.

Dogan et al., "Effect of depot oral cholecalciferol treatment on secondary hyperparathyroidism in stage 3 and stage 4 chronic kidney diseases patients," *Ren Fail.*, 30: 407-410 (2008).

Drueke et al., Recurrence of hyperparathyroidism from autografted parathyroid fragments in uremic patients in spite of administration of 25(OH)D3 and 1 a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).

Dusso et al, "Metabolic Clearance Rate and Production Rate of Calcitriol in Uremia," *Kidney Int.*, 35 860-864 (1989).

Dusso et al., "Extra-renal production of calcitriol in chronic renal failure," *Kidney Int.*, 34:368-375 (1988).

Dusso et al., "Extrarenal Production of Calcitrol in Normal and Uremic Humans," *Journal of Clinical Endocrinology and Metabolism*, 72(1):157-164 (1991).

Eastwood et al., "Biochemical and histological effects of 1,25 dihydroxycholecalciferol (1,25-DHCC) in the osteomalacia of chronic renal failure," *J Urol Nephrol (Paris,)* 80(12): 984-985 (1974).

Eastwood et al., "The contrasting effects on bone histology of vitamin D and of calcium carbonate in the osteomalacia of chronic renal failure," *Clin Sci Molec Med*, 47:23-42 (1974).

Eastwood et al., "The Effect of 25-Hydroxy Vitamin D3 in the Osteomalacia of Chronic Renal Failure," *Clin. Sci. Molec. Med.*, 52:499-508 (1977).

FDA's Guidance for Industry, Nonclinical Safety Evaluation of Drug or Biologic Combinations, Mar. 2006.

Fernandez et al., "Guidelines for Dosing of Intravenous Calcitriol in Dialysis Patients with Hyperparathyroidism," *Nephrol. Dial. Transplant.*, 11:96-101 (1996).

Fournier et al., "1-alpha-Hydroxycholecalciferol and 25-Hydroxycholecalciferol in Renal Bone Disease," *Calcified Tissues 1975: Proceedings of the 11th European Symposium on Calcified Tissues*, 226-235 (1975).

Fournier et al., "1α Hydroxycholecalciferol and 25 Hydroxycholecalciferol in Renal Bone Disease" Proc Eur Dial Transplant Assoc 12:227-236 (1976).

Fournier et al., "1α-hydroxycholecalciferol and 25-hydroxycholecalciferol in Renal Bone Disease" *Calcif Tissue Res.* 21:226-235 (1976).

Fournier et al., "Advances in Nephrology from the Necker Hospital" *Adv. Nephrol Necker Hosp.* 21:237-306 (1992).

Fournier et al., "Comparison of 1α-hydroxycholecalciferol and 25-hydroxycholecalciferol in the treatment of renal osteodystrophy: Greater effect of 25-hydroxycholecalciferol on bone mineralization" Kidney International 15:196-204 (1979).

Fournier et al., "Current Status of the Management of Renal Osteodystrophy" *Proceedings of the European Dialysis and Transplant Association* 15:547-568 (1978).

Fournier et al., "Impact of calcium and vitamin D therapy on arterial and cardiac disease in young adults with childhood-onset and stage renal disease," *Nephrol Dial Transplant*, 22:956-957 (2006).

Fournier et al., "Importance of Vitamin D Repletion in Uraemia," *Nephrol Dial Transplant*, 14(4):819-823 (1999).

Fournier et al., "Low doses of calcitriol or calcium carbonate for the prevention of hyperparathyroidism in predialysis patients?" *Nephrol Dial Transplant* 11 (7):1493-1495 (1996).

Fournier et al., "Present-Day Concepts in the Treatment of Chronic Renal Failure" *Contrib Nephrol.* 71:64-80 (1989).

Fournier et al., "Preventing Renal Bone Disease in Moderate Renal Failure with CaCO3 and 25(OH) Vitamin D3," *Kidney Int.*, 33:S178-S279 (1988).

Fournier et al., "Renal Osteodystrophy in Dialysis Patients: Diagnosis and Treatment," *Artificial Organs*, 22:530-557 (1998).

Fournier et al., "Renal Osteodystrophy: Pathophysiology and Treatment" *Hormone Res.* 20:44-58 (1984).

Fournier et al., "The Approach to the Treatment of Secondary Hyperparathyroidism in Early Renal Failure" *Am. J. Nephrol* 8:170-172 (1988).

Fournier et al., "Traitement vitaminique D et ostéodystrophies rénales: indications et modalités" *Nephrologie* 16(2)1 65-190 (1995) [journal in French]—abstract only.

Fournier, "Vitamin D: Biochemical, Chemical, and Clinical Aspects Related to Calcium Metabolism," Vitamin D: Proceedings of the Third Workshop on Vitamin D, Asilomar, Pacific Grove, CA, USA 667-669 (1977).

Friedman et al. "The Role of Vitamin D in Mild to Moderate Chronic Kidney Disease," *Trends in Endocrinology & Metab,.* 13(5):189-194 (2002).

Frohling et al., "Serum 25-hydroxyvitamin D in patients with chronic renal failure on long-term treatment with high doses of vitamin D2." *Nephron* 26: 116-120 (1980).

(56) References Cited

OTHER PUBLICATIONS

Frost et al., "Histomorphometric Changes in Trabecular Bone of Renal Failure Patients Treated with Calcifediol," *Metab. Bone Dis. & Rel. Res.*, 2:285-295 (1981).

Gallagher et al., "Comparison of the Histological Effect and Metabolism of 25-(OH)D and 1,25-(OH)2D in Rat Bone," p. 399-401, IN: Norman, *Vitamin D: Basic Research and its Clinical Application: Proceedings of the Fourth Workshop on Vitamin D*, Berlin, West Germany, Feb. 1979.

Ghazali et al., "Is low plasma 25-(OH) vitamin D a major risk factor for hyperparathyroidism and Looser's zones independent of calcitriol?" *Kidney International* 55:2169-2177 (1999).

Gibson, ed., Product optimisation. *Pharmaceutical Preformulation and Formulation: A Practical Guide from Candidate Drug Selection to Commercial Dosage Form*, 295-8 (2004).

Goodman, "Calcimimetic agents and secondary hyperparathyroidism: treatment and prevention," *Nephrol Dial Transplant*, 17:204-207 (2002).

Haddad et al., "Acute Administration of 25-Hydroxycholecalciferol in Man," *J. Clin. Endocrinol. Metab.*, 42:284-289 (1976).

Haddad et al., "Human Serum Binding Capacity and Affinity for 25-Hydroxyergocalciferol and 25-Hydroxycholecalciferol," *J. Clin. Endocrinol. Metab.*, 43:86-91 (1976).

Haddad et al., "Natural and Synthetic Sources of Circulating 25-Hydroxyvitamin D in Man," *Nature*, 244:515-517 (1973).

Haddad, "Plasma Vitamin D-binding Protein (Gc-Globulin): Multiple Tasks," *J. Steroid Biochem. Molec. Biol.*, 53:579-582 (1995).

Haddad, "Seasonal Diminution of Vitamin D Stores in the United States: Can Darker Winters Lead to Lighter Bones?" *Trends Endocrinol. Metab.*, 7:209-212 (1996).

Haddad, "Traffic, Binding and Cellular Access of Vitamin D Sterols," *Bone and Mineral Res.*, Elsevier, 5:281-308 (1987).

Haddad, "Vitamin D—Solar Rays, The Milky Way, or Both?" *NEJM*, 326:1213-1215 (1992).

Haldimann et al., "Effect of an Oral Dose of 25-Hydroxyvitamin D3 on Its Blood Levels in Patients with the Nephrotic Syndrome," *J Clin Endocrinology and Metabolism*, 50(3): 470-474 (1980).

Halloran et al., "Plasma Vitamin D Metabolite Concentrations in Chronic Renal Failure: Effect of Oral Administration of 25-Hydroxyvitamin D3," *J. Clin. Endocrin. & Metab.*, 59:1063-1069 (1984).

Hamida et al., "Hyperparathyroïdie secondaire ál insuffisance rénale" *Annales d'Endocrinologie* 55:147-158 (1994) [reference in French]—abstract only.

Hannula et al., "Constant, But Not Pulsed Calcitriol Suppresses Hemodialysis Patients' Antigen-Induced Lymphocyte Proliferation," *Nephron*, 86:139-144 (2000).

Hari et al., "Vitamin D insufficiency and effect of cholecalciferol in children with chronic kidney disease," *Pediatr.Nephrol,.* 25: 2483-2488 (2010).

Hay et al., "Vitamin D2 in Vertebrate Evolution," *Comp. Biochem. Physiol. B*, 56:375-380 (1977).

Hodson et al., "Treatment of childhood renal osteodystrophy with calcitriol or ergocalciferol," *Clin Nephrology*, 24(4): 192-200 (1985).

Holick, "Vitamin D Deficiency in CKD: Why Should We Care?" *Am. J. Kidney Dis.*, 45:1119-1121 (2005).

Holick, "Vitamin D Status: Measurement, Interpretation and Clinical Application," *Ann Epidemiol*, 19(2):73-78 (2009).

Hollis, "Circulating 25-Hydroxyvitamin D Levels Indicative of Vitamin D Sufficiency: Implications for Establishing a New Effective Dietary Intake Recommendation for Vitamin D," *J. Nutr.* 135: 317-322 (2005).

Horst et al., "A Sensitive Competitive Protein Binding Assay for Vitamin D in Plasma," *Steroids*, 37:581-592 (1981).

Horst et al., "Discrimination in the Metabolism of Orally Dosed Ergocalciferol and Cholecalciferol by the Pig, Rat and Chick," *Biochem. J.*, 204:185-189 (1982).

Horst et al., "Rat cytochrome P450C24 (CYP24) does not metabolize 1,25-dihydroxyvitamin D2 to calcitroic acid," *J. Cell Biochem.*, 88:282-285 (2003).

Hottelart et al., "Ostéodystrophie rénale (2): son traitement chez l'insuffisant rénal avant la dialyse" Nephrologie 21(6):275-282 (2000) [reference in French]—abstract only.

Houghton et al., "The Case Against Ergocalciferol (Vitamin D2) as a Vitamin Supplement," *Am. J. Clin. Nutr.*, 84:694-697 (2006).

Hunt, et al., "A Comparison of the Toxicity of Ergocalciferol and Cholecalciferol in Rhesus Monkeys (*Macaca mulatta*)," J. Nutrition, 102:975-986 (1972).

Hussar, "New Drugs of 1999," *J. Am. Pharmacist. Assoc.* 40(2):181-229 (2000).

International Search Report for Application No. PCT/US2007/061521, dated Jul. 17, 2007.

International Search Report for corresponding international application No. PCT/US2007/071791 (Feb. 5, 2008).

International Search Report and Written Opinion for PCT/US2008/061579 dated Aug. 21, 2008 (5 pages).

Ishimura et al., "Serum Levels of 1,25-Dihydroxyvitamin D, 24,25-Dihydroxyvitamin D, and 25-Hydroxyvitamin D in Nondialyzed Patients with Chronic Renal Failure," *Kidney Int.*, 55:1019-1027 (1999).

Jara et al., "Effect of Calcitriol Treatment and Withdrawal on Hyperparathyroidism in Haemodialysis Patients with Hypocalcaemia," *Nephrol. Dial. Transplant.*, 16:1009-1016 (2001).

Jean et al., "Daily Oral 25-Hydroxycholecalciferol Supplementation for Vitamin D Deficiency in Haemodialysis Patients: Effects on Mineral Metabolism and Bone Markers," *Nephrol. Dial. Transplant*, 23:3670-3676 (2008).

Jean et al., "Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment" *Nephron. Clin. Pract.* 110:c58-c65 (2008).

Jean et al., "Monthly cholecalciferol administration in heamodialysis patients: a simple and efficient strategy for vitamin D supplementation" *Nephrol. Dial. Transplant* 24(12):3799-3805 (2009).

Jones, "Pharmacokinetics of vitamin D toxicity," *Am. J. Clin. Nutr.* 88(suppl): 582S-6S (2008).

Jones, "Why dialysis patients need combination therapy with both cholecalciferol and a calcitriol analogs," *Seminars in Di alysis*, pp. 1-5 (2010).

Jones., "Expanding the Role for Vitamin D in Chronic Kidney Disease: Importance of Blood 25-OH-D Levels and Extra-Renal 1α-Hydroxyase in the Classical and Nonclassical Actions of 1α, 25-Dihydroxyvitamin D3," *Seminars in Dialysis*, 20(4):316-324 (2007).

Kajihara et al., "Novel Method to Control Release of Lipophilic Drugs with High Potency from Silicone," *Chem. Pharm. Bull.*, 51:11-14 (2003).

Kalantar-Zadeh et al., "Clinical Outcomes with Active versus Nutritional Vitamin D Compounds in Chronic Kidney Disease" *Clin J Am Soc Nephrol*. 4(9):1529-1539 (2009).

Kanis et al., "Rate of Reversal of Hypercalcaemia and Hypercalciuria Induced by Vitamin D and Its 1-alpha-Hydroxylated Derivatives," *BMJ*, 1:78-81 (1977).

Kim, *Advanced Pharmaceutics: Physicochemical Principles*, pp. 362-392, Boca Raton, Fla: CRC Press (2004).

Kleinman et al., "Effects of Calcifediol on Calcified Tissue in Uremia," *Arch Intern Med*, 138: 864-865 (1978).

Kobayashi et al., "2β-(3-Hydroxyproxy)-α,25-Dihydroxyvitamin D3 (ED-71), Preventive and Therapeutic Effects on Bone Mineral Loss in Ovariectomized Rats," *Bioorganic & Medicinal Chemistry Letters*, 3(9):1815-1819 (1993).

Kooienga et al., "The effect of combined calcium and vitamin D3 supplementation on serum intact parathyroid hormone in moderate CKD," *Am.J.Kidney Dis,*. 53: 408-416 (2009).

Koshikawa et al., "Clinical effect of intravenous calcitrol administration on secondary hyperparathyroidism. A double-blind study among 4 doses", *Nephron*, 90:413-423 (2002).

LaClair et al., "Prevalence of Calcidiol Deficiency in CKD: A Cross-Sectional Study Across Latitudes in the United States," *Am. J. Kidney Dis.*, 45:1026-1033 (2005).

(56) References Cited

OTHER PUBLICATIONS

Lafage et al., "Ketodiet, Physiological Calcium Intake and Native Vitamin D Improve Renal Osteodystrophy," *Kidney Int.*, 42:1217-1225 (1992).
Lambert et al., "Evidence for Extranrenal Production of 1-alpha,25-Dihydroxyvitamin D in Man," *J. Clin. Invest.*, 69:722-725 (1982).
Lambrey et al., "24, 25 Dihydroxycalciferol: Assay in Non-Anephric Patients on Chronic Haemodialysis and Assessment of its Possible Pathophysiological Role in Renal Osteodystrophy" *Proc Eur Dial Transplant Assoc.* 17:548-556 (1980).
Langman et al., "25-Hydroxyvitamin D3 (Calcifediol) Therapy of Juvenile Renal Osteodystrophy: Beneficial Effect on Linear Growth Velocity," *J. Pediatrics*, 100:815-820 (1982).
Larrosa M. et al., Long-Term Treatment of Hypovitaminosis D. Calcidol or Cholecalciferol? *Annals of the Rheumatic Diseases*, vol. 64, No. Suppl. 3, Jul. 2005, p. 366.
Lau et al., "Vitamin D Therapy of Osteoporosis: Plain Vitamin D Therapy Versus Active Vitamin D Analog (D-Hormone) Therapy," *Calcif. Tissue Int.*, 65:295-306 (1999).
Lehmann et al., "Coating of Tablets and Small Particles with Acrylic Resins by Fluid Bed Technology," *Int. J. Pharm. Tech. & Prod. Mfr.*, 2:31-43 (1981).
Letteri et al., "Effects of 25-Hydroxycholecalciferol on Calcium Metabolism in Chronic Renal Failure" Adv. Exp. Med. Biol. 81:591-601 (1977).
Lips et al., "A Global Study of Vitamin D Status and Parathyroid Function in Postmenopausal Women with Osteoporosis: Baseline Data from the Multiple Outcomes of Raloxifene Evaluation Clinical Trial," *The Jour. of Clin. Endo. & Meta.*, 86(3):1212-1221 (2001).
Lomonte et al., "Are Low Plasma Levels of 25-(OH) Vitamin D a Major Risk Factor for Hyperparathyroidism Independent of Calcitriol in Renal Transplant Patients?" *J. Nephrol.*, 18:96-101 (2005).
Lund et al., "Serum 1,25-Dihydroxycholecalciferol in Anephric. Haemodialyzed and Kidney-transplanted Patients," *Nephron*, 25:30-33 (1980).
Maierhofer et al., "Synthesis and Metabolic Clearance of 1,25-Dihydroxyvitamin D as Determinants of Serum Concentrations: a Comparison of Two Methods" Journal of Clinical Endocrinology and Metabolism 53:472-475 (1981).
Manni et al., "Oral Calcitriol: Comparison Between the Same Weekly Dose Administered as a Single vs. Two Divided Pulsed Doses in Secondary Hyperparathyroidism of Chronic Renal Failure," *Ital. J Mineral Electrolyte Metab.*, 11:61-64 (1997).
Matsushita et al., "Clinical effects of 25-hydroxycholecalciferol in patients with chronic renal failure," *J Nutr Sci Vitaminol*, 23:257-261 (1977).
Mazouz et al., "Risk factors of renal failure progression two years prior to dialysisis" *Clinical Nephrology* 51(6):355-366 (1999).
Mazur, "Effects of 25-OHD3 on Renal Function in Pediatric Patients with Chronic Renal Failure," *Mineral Electrolyte Metab.* 10:351-358 (1984).
Memmos et al., "Response of uremic osteoid to vitamin D," *Kidney Int*, 21(Suppl. 11): S50-S54 (1982).
Menon et al., "Vitamin D insufficiency and hyperparathyroidism in children with chronic kidney disease," Pedaitr Nephrol, 23:1831-1836 (2008).
Messa et al., "Direct In Vivo Assessment of Parathyroid Hormone-Calcium Relationship Curve in Renal Patients," *Kidney Int.*, 46:1713-1720 (1994).
Moe et al., "A randomized trial of cholecalciferol versus doxercalciferol for lowering parathyroid hormone in chronic kidney disease," *Clin.J.Am.Soc.Nephrol*. 5: 299-306 (2010).
Moe et al., "Safety and Efficacy of Pulse and Daily Calcitriol in Patients on CAPD: A Randomized Trial," *Nephrol. Dial. Transplant.*, 13:1234-1241 (1998).
Morris, "Vitamin D: A Hormone for All Seasons—How Much is Enough?" *Clin. Biochem. Rev.*, 26:21-32 (2005).
Muindi et al., "Phamacokinetics of Liquid Calcitriol Formulation in Advanced Solid Tumor Patients: Comparison with Caplet Formulation," *Cancer Chemother. Pharmacol.*, 56:492-496 (2005).
Naik et al., "Effects of Vitamin D Metabolites and Analogues on Renal Function," *Nephron*, 28:17-25 (1981).
Nakanishi et al., "The Roles of Vitamin D in Secondary Hyperparathyroidism," [journal in Japanese] 52:1107-1112 (2004).
Norman et al. (eds.), *Vitamin D—Gene Regulation, Structure-Function Analysis and Clinical Application: Proceedings of the Eighth Workshop on Vitamin d Paris, France*, pp. 765-766, New York: Walter De Gruyter Inc. (1991).
Oksa et al., "Effects of long-term cholecalciferol supplementation on mineral metabolism and calciotropic hormones in chronic kidney disease," *Kidney Blood Press Res.*, 31: 322-329 (2008).
Parfitt et al., "Calcitriol But No Other Metabolite of Vitamin D is Essential for NormalBone Growth and Development in the Rat," *J. Clin. Invest.*, 73:576-586 (1984).
Peacock et al., "Effect of Calcium or 25OH Vitamin D3 Dietary Supplementation on Bone Loss at the Hip in Men and Women over the Age of 60" *The Journal of Clinical Endocrinology & Metabolism*, 85(9):3011-3019 (2007).
Phadnis et al., "Direct, Rapid Effects of 25-Hydroxyvitamin D3 on Isolated Intestinal Cells," *J. Cell. Biochem.*, 90:287-293 (2003).
Pourgholami et al., "1, 25-Dihydroxyvitamin D3 Dissolved in Lipiodol Produces a Sustained Antiproliferative Effect in the Human Hepatoblastoma Cell Line HepG2," *Anticancer Res.*, 20:723-728 (2000).
Pourgholami et al., "In Vitro Antiproliferative Activity of a Medium-Chain Triglyceride Solution of 1, 25-Dihydroxyvitamin D3 in HepG2 Cells," *Anticancer Res.*, 20:4257-4260 (2000).
Rapuri, P.B. et al., "Effect of Vitamins D2 and D3 Supplement Use on Serum 25-OHD Concentration in Elderly Women in Summer and Winter," Calcified Tissue International, 74(2):150-156 (2004).
Recker et al., "The Efficacy of Calcifediol in Renal Osteodystrophy," *Arch. Intern. Med.*, 138:857-863 (1978).
Reddy et al., *Abstracts Sixth Annual Scientific Meeting of the American Society for Bone and Mineral Research*, 36:524 (1984).
Reichel et al., "Calcium Metabolism in Early Chronic Renal Failure: Implications for the Pathogenesis of Hyperparathyroidism," *Nephrol. Dial. Transplant.*, 6:162-169 (1991).
Reichel et al., "Intermittent Versus Continuous Administration of 1,25-dihydroxyvitamin D3 in experimental renal hyperparathyroidism," *Kidney Int.*, 44:1259-1265 (1993).
Reichel, "Current treatment options in secondary renal hyperparathyroidism," *Nephrol Dial Transplant* 21:23-28 (2006).
Ritter et al., "25-Hydroxyvitamin D3 suppresses PTH synthesis and secretion by bovine parathyroid cells," *Kidney Int.*, 70:654-659 (2006).
Rocaltrol® Complete Product Information, Roche, Jul. 27, 2004.
Rucker et al., "Vitamin D insufficiency and treatment with oral vitamin D3 in northern-dwelling patients with chronic kidney disease," *J.Nephrol*. 22: 75-82 (2009).
Russell et al., "Therapeutic Effects of 25-Hydroxyvitamin D3 on Renal Osteodystrophy," *Mineral Electrolyte Metab.*, 1:129-138 (1978).
Rutherford et al., "Effect of 25-Hydroxycholecalciferol on Calcium Absorption in Chronic Renal Disease," Kidney International, 8:320-324 (1975).
Saab et al., "Prevalence of Vitamin D Deficiency and the Safety and Effectiveness of Monthly Ergocalciferol in Hemodialysis Patients," *Nephron Clin. Pract*., 105:c132-c138 (2007).
Sanchez, "Prevention and Treatment of Renal Osteodystrophy in Children With Chronic Renal Insufficiency and End-Stage Renal Disease," *Seminars in Nephrology*, 21:441-450 (2001).
Sebert et al. "Comparative effects of equal doses of vitamin D2 and vitamin D3 for the correction of vitamin D deficiency in the elderly" in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Sebert et al., "Effets a Long Terme D'Une Association De 25-Hydroxycholécalciférol et de 1-Alpha-Hydroxycholécalciférol

(56) References Cited

OTHER PUBLICATIONS

Sur L'Ostéodystrophie Des Hémodialysés Chroniques" Rev. Rhum Mal Osteoartic 48(7-9):535-541 (1981).
Sebert et al., "Limit by Hyperphosphatemia of the Usefulness of Vitamin D Metabolites (1 alpha-Hydroxycholecalciferol and 25-Hydroxycholecalciferol) in the Treatment of Renal Osteodystrophy," *Metab. Bone Dis. & Rel. Res.*, 2:217-222 (1980).
Sekkarie, "The Impact of Over-the-counter Vitamin D Supplementals on Vitamin D and Parathyroid Hormone Levels in Chronic Kidney Disease," *Clin. Nephrology*, 65:91-96 (2006).
Shah et al., "Prevalence and correction of 25(OH) vitamin D deficiency in peritoneal dialysis patients," *Peritoneal Dialysis Int.*, 25:362-366 (2005).
Sjoden, et al., "1α-Hydroxyvitamin D2 is Less Toxic than 1α-Hydroxyvitamin D3 in the Rat," Society for Experimental Biology and Medicine, 179: 432-436 (1985).
Skelly et al., In vitro and in vivo testing an correlation for oral controlled/modified-release dosage forms. *Pharm. Res.*, 7(9):975-82 (1990).
Somerville et al., "Resistance to Parathyroid Hormone in Renal Failure: Role of Vitamin D Metabolites," *Kidney Int.*, 14:245-254 (1978).
Sommerfeldt et al., "Metabolism of Orally Administered [3H]Ergocalciferol and [3H]Cholecalciferol by Dairy Calves," *J. Nutr.*, 113:2595-2600 (1983).
Stamp et al., "Comparison of Oral 25-Hydroxycholecalciferol, Vitamin D, and Ultraviolet Light as Determinants of Circulating 25-Hydroxyvitamin D," *The Lancet*, 1341-1343 (Jun. 25, 1977).
Stein et al., "An Update on the Therapeutic Potential of Vitamin D Analogues," *Expert Opin. Investig. Drugs*, 12:825-840 (2003).
Stubbs et al., "Cholecalciferol supplementation alters calcitriol-responsive monocyte proteins and decreases inflammatory cytokines in ESRD," J.Am.Soc.Nephrol., 21: 353-361 (2010).
Stumpf, "The Dose Makes the Medicine," *Drug Discovery Today*, 11:550-555 (2006).
Szycher, *Szycher's Dictionary of Biomaterials and Medical Devices*, pp. 20, 48, 127, Lancaster, Penn: Technomic Publishing Co., Inc. (1992).
Sömjen et al., "Nonhypercalcemic Analogs of Vitamin D Stimulate Creatine Kinase B Activity in Osteoblast-Like ROS 17/2.8 Cells and Up-Regulate Their Responsiveness to Estrogens," *Steroids*, 63:340-343 (1998).
Taylor and Norman, "Interrelationship of Serum 25-Hydroxyvitamin D3 and 1,25-Dihydroxyvitamin D in Juvenile Renal Osteodystrophy after Therapy with 25-Hydroxyvitamin D3" Metab. Bone Dis. & Rel. Res. 4:255-261 (1982).
Taylor et al., "Interrelationship of Serum 25-Hydroxyvitamin D3 and 1,25-Dihydroxyvitamin D in Juvenile Renal Osteodystrophy after Therapy with 25-Hydroxyvitamin D3," *Metab. Bone Dis. & Rel. Res.*, 4:255-261 (1982).
Taylor et al., "The absence of 24,25-dihydroxycholecalciferol in anephric patients," *Clin.Sci.Mol.Med.Suppl.*, 55: 541-547 (1978).
Taylor, CM, 24,25-Dihydroxyvitamin D in Human Serum. In: Vitamin D. Basic Research and Clinical Applications, pp. 197-203. Walter de Gruyter, New York (1979).
Teitelbaum et al., "Calcifediol in Chronic Renal Insufficiency" *JAMA* 235(2):164-167 (1976).
Teitelbaum et al., "Tetracycline fluorescence in uremic and primary hyperparathyroid bone," *Kidney Int.*, 12:366-372 (1977).
Thomas et al., "Hypovitaminosis D in Medical Inpatients," *NEJM*, 338:777-783 (1998).
Thombre, "Assessment of the feasibility of oral controlled release in an exploratory development setting," *Drug Discovery Today*, 10(17): 1159-1166 (2005).
Tokmak et al., "High-dose cholecalciferol to correct vitamin D deficiency in haemodialysis patients," *Nephrol.Dial.Transplant.*, 23: 4016-4020 (2008).
Trakarnvanich et al., "Effect of high dose ergocalciferol in chronic kidney disease patients with 25-hydroxyvitamin D deficiency," *J.Med.Assoc.Thai*. 93: 885-891 (2010).
van Boxtel et al., Drug Benefits and Risks, International Textbook of Clinical Pharmacology, (2001).
Van Weelden et al., "Apoptotic Regression of MCF-7 Xenografts in Nude Mice Treated with the Vitamin D3 Analog, EB1089," *Endocrinology*, 139:2102-2110 (1998).
Verberckmoes et al., "Osteodystrophy of Dialysed Patients Treated with Vitamin D," *Proc Eur Dial Transplant Assoc.*, 10(0): 217-226 (1973).
Vieth, "What is the optimal vitamin D status for health?" *Prog. Biophys. Mol. Biol.*, 92:26-32 (2006).
Wise (ed.), *Handbook of Pharmaceutical Controlled Release Technology*, "An Overview of Controlled Release Systems," Chapter 22, pp. 431-445, 461-463; Research and Development Aspects of Oral Controlled-Release Dosage Forms, Chapter 23, pp. 465-473, New York: Marcel Dekker, Inc. 3 (2000).
Witmer et al., "Effects of 25-hydroxycholecalciferol on bone lesions of children with terminal renal failure" *Kidney International* 10:395-408 (1976).
Written Opinion of counterpart PCT/US2008/061579 dated Aug. 21, 2008 (6 pages).
Written Opinion of the International Searching Authority for corresponding international application No. PCT/US2007/071791 (Feb. 5, 2008).
Zerwekh et al., "Extra-Renal Production of 24,25-Dihydroxyvitamin D in Chronic Renal Failure During 25 Hydroxyvitamin D3 Therapy," *Kidney Int.*, 23:401-406 (1983).
Zisman et al., "Impact of Ergocalciferol Treatment of Vitamin D Deficiency on Serum Parathyroid Hormone Concentrations in Chronic Kidney Disease," *Am. J. Nephrol.*, 27:36-43 (2007).
Zucchelli et al., "Therapeutic effects of 25-hydroxycholecalciferol and sodium etidronate on renal osteodystrophy," *Mineral.Electrolyte Metab*. 7: 86-96 (1982).
Henry et al., Response of chick parathyroid glands to the vitamin D metabolites, 1,25-dihydroxycholecalciferol and 24,25-dihydroxycholecalciferol, *J. Nutr.*, 107(10):1918-26 (1977).
Office Action (with English translation), Japanese patent application No. 2014-031369, dated Mar. 9, 2015.

METHOD OF TREATING AND PREVENTING SECONDARY HYPERPARATHYROIDISM

This is a continuation of U.S. patent application Ser. No. 12/305,572 filed Mar. 2, 2009, which is the National Phase of International Application No. PCT/US2007/071791 filed Jun. 21, 2007, which claims the benefit of priority under 35 U.S.C. §119(e) of U.S. Provisional Patent Application Ser. No. 60/815,148 filed Jun. 21, 2006. The disclosure of each priority application is incorporated herein by reference.

BACKGROUND

1. Field of the Disclosure

The disclosure relates generally to Vitamin D repletion and active Vitamin D hormone replacement. More particularly, the disclosure relates to methods of treating elevated blood levels of intact parathyroid hormone (iPTH), such as in secondary hyperparathyroidism, by increasing or maintaining blood concentrations of both 25-hydroxyvitamin D and 1,25-dihydroxyvitamin D in a patient by administering, as necessary, both Vitamin D repletion and Vitamin D hormone replacement therapies.

2. Brief Description of Related Technology

Secondary hyperparathyroidism is a disorder which develops primarily because of Vitamin D deficiency. It is characterized by abnormally elevated blood levels of parathyroid hormone (PTH) and, in the absence of early detection and treatment, it becomes associated with parathyroid gland hyperplasia and a constellation of metabolic bone diseases. It is a common complication of chronic kidney disease (CKD), with rising incidence as CKD progresses. Secondary hyperparathyroidism can also develop in individuals with healthy kidneys, due to environmental, cultural or dietary factors which prevent adequate Vitamin D supply.

"Vitamin D" is a term that refers broadly to the organic substances named Vitamin $D_2$, Vitamin $D_3$, Vitamin $D_4$, etc., and to their metabolites and hormonal forms that influence calcium and phosphorus homeostasis. "Vitamin D deficiency" is a term that broadly refers to reduced or low blood levels of Vitamin D, as defined immediately above.

The most widely recognized forms of Vitamin D are Vitamin $D_2$ (ergocalciferol) and Vitamin $D_3$ (cholecalciferol). Vitamin $D_2$ is produced in plants from ergosterol during sunlight exposure and is present, to a limited extent, in the human diet. Vitamin $D_3$ is generated from 7-dehydrocholesterol in human skin during exposure to sunlight and also is found, to a greater extent than Vitamin $D_2$, in the human diet, principally in dairy products (milk and butter), certain fish and fish oils, and egg yolk. Vitamin D supplements for human use consist of either Vitamin $D_2$ or Vitamin $D_3$.

Both Vitamin $D_2$ and Vitamin $D_3$ are metabolized into prohormones by one or more enzymes located in the liver. The involved enzymes are mitochondrial and microsomal cytochrome P450 (CYP) isoforms, including CYP27A1, CYP2R1, CYP3A4, CYP2J3 and possibly others. These enzymes metabolize Vitamin $D_2$ into two prohormones known as 25-hydroxyvitamin $D_2$ and 24(S)-hydroxyvitamin $D_2$, and Vitamin $D_3$ into a prohormone known as 25-hydroxyvitamin $D_3$. The two 25-hydroxylated prohormones are more prominent in the blood, and are collectively referred to as "25-hydroxyvitamin D". Vitamin $D_2$ and Vitamin $D_3$ can be metabolized into these same prohormones outside of the liver in certain epithelial cells, such as enterocytes, which contain the same (or similar) enzymes, but extrahepatic prohormone production probably contributes little to blood levels of 25-hydroxyvitamin D.

The rates of hepatic and extrahepatic production of the Vitamin D prohormones are not tightly regulated, and they vary mainly with intracellular concentrations of the precursors (Vitamin $D_2$ and Vitamin $D_3$). Higher concentrations of either precursor increase prohormone production, while lower concentrations decrease production. Hepatic production of prohormones is inhibited by high levels of 25-hydroxyvitamin D via a poorly understood mechanism apparently directed to prevention of excessive blood prohormone levels.

The Vitamin D prohormones are further metabolized in the kidneys into potent hormones by an enzyme known as CYP27B1 (or 25-hydroxyvitamin $D_3$-1α-hydroxylase) located in the proximal kidney tubule. The prohormones 25-hydroxyvitamin $D_2$ and 24(S)-hydroxyvitamin $D_2$ are metabolized into hormones known as 1α,25-dihydroxyvitamin $D_2$ and 1α,24(S)-dihydroxyvitamin $D_2$. Likewise, 25-hydroxyvitamin $D_3$ is metabolized into a hormone known as 1α,25-dihydroxyvitamin $D_3$ (or calcitriol). These hormones are released by the kidneys into the blood for systemic delivery. The two 25-hydroxylated hormones, usually far more prominent in the blood than 1α,24(S)-dihydroxyvitamin $D_2$, are collectively referred to as "1,25-dihydroxyvitamin D". Vitamin D prohormones can be metabolized into hormones outside of the kidneys in keratinocytes, lung epithelial cells, enterocytes, cells of the immune system (e.g., macrophages) and certain other cells containing CYP27B1 or similar enzymes, but such extrarenal hormone production is incapable of sustaining normal blood levels of 1,25-dihydroxyvitamin D in advanced CKD.

Blood levels of 1,25-dihydroxyvitamin D are precisely regulated by a feedback mechanism which involves PTH. The renal 1α-hydroxylase (or CYP27B1) is stimulated by PTH and inhibited by 1,25-dihydroxyvitamin D. When blood levels of 1,25-dihydroxyvitamin D fall, the parathyroid glands sense this change via intracellular Vitamin D receptors (VDR) and secrete PTH. The secreted PTH stimulates expression of renal CYP27B1 and, thereby, increases production of Vitamin D hormones. As blood concentrations of 1,25-dihydroxyvitamin D rise again, the parathyroid glands attenuate further PTH secretion. As blood PTH levels fall, renal production of Vitamin D hormones decreases. Rising blood levels of 1,25-dihydroxyvitamin D also directly inhibit further Vitamin D hormone production by CYP27B1. PTH secretion can be abnormally suppressed in situations where blood 1,25-dihydroxyvitamin D concentrations become excessively elevated, as can occur in certain disorders or as a result of bolus doses of Vitamin D hormone replacement therapies. Oversuppression of PTH secretion can cause or exacerbate disturbances in calcium homeostasis. The parathyroid glands and the renal CYP27B1 are so sensitive to changes in blood concentrations of Vitamin D hormones that serum 1,25-dihydroxyvitamin D is tightly controlled, fluctuating up or down by less than 20% during any 24-hour period. In contrast to renal production of Vitamin D hormones, extrarenal production is not under precise feedback control.

The Vitamin D hormones have essential roles in human health which are mediated by the intracellular VDR. In particular, the Vitamin D hormones regulate blood calcium levels by controlling intestinal absorption of dietary calcium and reabsorption of calcium by the kidneys. The Vitamin D hormones also participate in the regulation of cellular differentiation and growth and normal bone formation and metabolism. Further, Vitamin D hormones are required for the normal functioning of the musculoskeletal, immune and renin-angiotensin systems. Numerous other roles for Vitamin D hormones are being postulated and elucidated, based on the documented presence of intracellular VDR in nearly every human tissue.

The actions of Vitamin D hormones on specific tissues depend on the degree to which they bind to (or occupy) the intracellular VDR in those tissues. The three Vitamin D hormones $1\alpha,25$-dihydroxyvitamin $D_2$, $1\alpha,24(S)$-dihydroxyvitamin $D_2$, and $1\alpha,25$-dihydroxyvitamin $D_3$ have nearly identical affinities for the VDR and, therefore, have essentially equivalent VDR binding when present at the same intracellular concentrations. VDR binding increases as the intracellular concentrations of the hormones rise, and decreases as the intracellular concentrations fall. In all cells, intracellular concentrations of the Vitamin D hormones change in direct proportion to changes in blood hormone concentrations. In cells containing CYP27B1 (or similar enzymes), intracellular concentrations of the Vitamin D hormones also change in direct proportion to changes in blood and/or intracellular prohormone concentrations, as discussed above.

Vitamin $D_2$, Vitamin $D_3$ and their prohormonal forms have affinities for the VDR which are estimated to be at least 100-fold lower than those of the Vitamin D hormones. As a consequence, physiological concentrations of these hormone precursors exert little, if any, biological actions without prior metabolism to Vitamin D hormones. However, supraphysiological levels of these hormone precursors, especially the prohormones, in the range of 10 to 1,000 fold higher than normal, can sufficiently occupy the VDR and exert actions like the Vitamin D hormones.

Blood levels of Vitamin $D_2$ and Vitamin $D_3$ are normally present at stable, concentrations in human blood, given a sustained, adequate supply of Vitamin D from sunlight exposure and an unsupplemented diet. Slight, if any, increases in blood Vitamin D levels occur after meals since unsupplemented diets have low Vitamin D content, even those containing foods fortified with Vitamin D. The Vitamin D content of the human diet is so low that the National Institutes of Health (NIH) cautions "it can be difficult to obtain enough Vitamin D from natural food sources" [NIH, Office of Dietary Supplements, Dietary Supplement Fact Sheet: Vitamin D (2005)]. Almost all human Vitamin D supply comes from fortified foods, exposure to sunlight or from dietary supplements, with the last source becoming increasingly important. Blood Vitamin D levels rise only gradually, if at all, after sunlight exposure since cutaneous 7-dehydrocholesterol is modified by UV radiation to pre-Vitamin $D_3$ which undergoes thermal conversion in the skin to Vitamin $D_3$ over a period of several days before circulating in the blood.

Blood Vitamin D hormone concentrations also remain generally constant through the day in healthy individuals, but can vary significantly over longer periods of time in response to seasonal changes in sunlight exposure or sustained alterations in Vitamin D intake. Marked differences in normal Vitamin D hormone levels are commonly observed between healthy individuals, with some individuals having stable concentrations as low as approximately 20 pg/mL and others as high as approximately 70 pg/mL. Due to this wide normal range, medical professionals have difficulty interpreting isolated laboratory determinations of serum total 1,25-dihydroxyvitamin D; a value of 25 pg/mL may represent a normal value for one individual or a relative deficiency in another.

Transiently low blood levels of 1,25-dihydroxyvitamin D stimulate the parathyroid glands to secrete PTH for brief periods ending when normal blood Vitamin D hormone levels are restored. In contrast, chronically low blood levels of 1,25-dihydroxyvitamin D continuously stimulate the parathyroid glands to secrete PTH, resulting in a disorder known as secondary hyperparathyroidism. Chronically low hormone levels also decrease intestinal calcium absorption, leading to reduced blood calcium concentrations (hypocalcemia) which further stimulate PTH secretion. Continuously stimulated parathyroid glands become increasingly hyperplastic and eventually develop resistance to regulation by vitamin D hormones. Without early detection and treatment, secondary hyperparathyroidism progressively increases in severity, causing debilitating metabolic bone diseases, including osteoporosis and renal osteodystrophy.

Chronically low blood levels of 1,25-dihydroxyvitamin D develop when there is insufficient renal CYP27B1 to produce the required supply of Vitamin D hormones, a situation which commonly arises in CKD. The activity of renal CYP27B1 declines as glomerular filtration rate (GFR) falls below approximately 60 ml/min/1.73 $m^2$ due to the loss of functioning nephrons. In end-stage renal disease (ESRD), when the kidneys fail completely and hemodialysis is required for survival, renal CYP27B1 often becomes altogether absent. Any remaining CYP27B1 is greatly inhibited by elevated serum phosphorous (hyperphosphatemia) caused by inadequate renal excretion of dietary phosphorous.

Chronically low blood levels of 1,25-dihydroxyvitamin D also develop because of a deficiency of Vitamin D prohormones, since renal hormone production cannot proceed without the required precursors. Prohormone production declines markedly when cholecalciferol and ergocalciferol are in short supply, a condition often described by terms such as "Vitamin D insufficiency", "Vitamin D deficiency" or "hypovitaminosis D." Therefore, measurement of 25-hydroxyvitamin D levels in blood has become the accepted method among healthcare professionals to monitor Vitamin D status. Recent studies have documented that the great majority of CKD patients have low blood levels of 25-hydroxyvitamin D, and that the prevalence of Vitamin D insufficiency and deficiency increases as CKD progresses.

It follows that individuals most vulnerable to developing chronically low blood levels of 1,25-dihydroxyvitamin D are those with CKD. Most CKD patients typically have decreased levels of renal CYP27B1 and a shortage of 25-hydroxyvitamin D prohormones. Not surprisingly, most CKD patients develop secondary hyperparathyroidism. Unfortunately, early detection and treatment of secondary hyperparathyroidism in CKD is rare, let alone prevention.

The National Kidney Foundation (NKF) has recently focused the medical community's attention on the need for early detection and treatment of secondary hyperparathyroidism by publishing Kidney Disease Outcomes Quality Initiative (K/DOQI) Clinical Practice Guidelines for Bone Metabolism and Disease in Chronic Kidney Disease [Am. J. Kidney Dis. 42:S1-S202, 2003)]. The K/DOQI Guidelines identified the primary etiology of secondary hyperparathyroidism as chronically low blood levels of 1,25-dihydroxyvitamin and recommended regular screening in CKD Stages 3 through 5 for elevated blood PTH levels relative to stage-specific PTH target ranges. CKD Stage 3 was defined as moderately decreased kidney function (GFR of 30-59 mL/min/1.73 $m^2$) with an intact PTH (iPTH) target range of 30-70 pg/mL; Stage 4 was defined as severely decreased kidney function (GFR of 15-29 mL/min/1.73 $m^2$), with an iPTH target range of 70-110 pg/mL; and Stage 5 was defined as kidney failure (GFR of <15 mL/min/1.73 $m^2$ or dialysis) with an iPTH target range of 150-300 pg/mL. In the event that screening revealed an iPTH value to be above the target range for the stage of CKD (Stage 3 or 4), the Guidelines recommended a follow-up evaluation of serum total 25-hydroxyvitamin D to detect possible Vitamin D insufficiency or deficiency. If 25-hydroxyvitamin D below 30 ng/mL was observed, the recommended intervention was Vitamin D repletion therapy using orally administered ergocalciferol. If 25-hydroxyvitamin D above 30 ng/mL was observed, the recommended intervention was Vitamin D hormone replacement therapy using oral or intravenous Vitamin D hormones or analogues. The Guidelines did not recommend the concurrent application of Vitamin D repletion and Vitamin D hormone replacement therapies, consistent with warnings mandated by the Food and Drug Administration in package inserts for Vitamin D hormone replacement products.

The NKF K/DOQI Guidelines defined Vitamin D sufficiency as serum 25-hydroxyvitamin D levels≥30 ng/mL. Recommended Vitamin D repletion therapy for patients with "Vitamin D insufficiency", defined as serum 25-hydroxyvitamin D of 16-30 ng/mL, was 50,000 IU per month of oral Vitamin $D_2$ for 6 months, given either in single monthly doses or in divided doses of approximately 1,600 IU per day. Recommended repletion therapy for patients with "Vitamin D deficiency" was more aggressive: for "mild" deficiency, defined as serum 25-hydroxyvitamin D of 5-15 ng/mL, the Guidelines recommended 50,000 IU per week of oral Vitamin $D_2$ for 4 weeks, followed by 50,000 IU per month for another 5 months; for "severe" deficiency, defined as serum 25-hydroxyvitamin D below 5 ng/mL, the Guidelines recommended 50,000 IU/week of oral Vitamin $D_2$ for 12 weeks, followed by 50,000 IU/month for another 3 months. Doses of 50,000 IU per week are approximately equivalent to 7,000 IU per day.

The K/DOQI Guidelines recommended currently available oral Vitamin D products, especially those containing Vitamin $D_2$, for achieving and maintaining optimal blood 25-hydroxyvitamin D levels. Unfortunately, these preparations are far from ideal for use in CKD patients, and can be altogether ineffective based on recently published clinical investigations. They typically contain 400 IU to 5,000 IU of Vitamin $D_3$ or 50,000 IU of Vitamin $D_2$ and are formulated for quick or immediate release in the gastrointestinal tract. When administered at chronically high doses, as is usually required for repletion, these products have significant and, often, severe limitations. They produce pharmacological concentrations of Vitamin D in the lumen of the duodenum which promote catabolism of Vitamin D by 26- hydroxylation in the local enterocytes, causing decreased systemic bioavailability and supraphysiological surges in blood Vitamin D levels. Such surges are undesirable because they promote storage of Vitamin D in adipose tissue, which is less available for later hepatic conversion to 25-hydroxyvitamin D, and hepatic catabolism of Vitamin D. Further, they cause abrupt increases in blood and intracellular 25-hydroxyvitamin D levels, thereby promoting marked catabolism of both Vitamin D and 25-hydroxyvitamin D by 24-and/or 26-hydroxylation in the kidney and other tissues, down-regulation of hepatic production of Vitamin D prohormones, unnecessarily impeding the efficient repletion of Vitamin D insufficiency or deficiency, and local aberrations in calcium and phosphorus homeostasis mediated by direct binding to VDR.

All but two FDA-approved "quick-release" high unit dose (50,000 IU) prescription formulations of Vitamin $D_2$, considered by the NKF Clinical Practice Guidelines to be potentially safer than Vitamin $D_3$, have been discontinued from the U.S. market because of poor acceptance by healthcare professionals. Administration of 25-hydroxyvitamin $D_3$ in an immediate release oral formulation has been tried as an alternative method of Vitamin D supplementation. This approach, which has been subsequently abandoned, caused problems as do the currently used Vitamin D supplements. Specifically, administration of 25-hydroxyvitamin $D_3$ produced surges or spikes in blood and intracellular 25-hydroxyvitamin D levels, thereby promoting (a) competitive displacement of Vitamin D hormones from the serum Vitamin D Binding Protein (DBP) and excessive delivery of the displaced hormones to tissues containing VDR, and (b) transiently excessive renal and extrarenal production of Vitamin D hormones, which together led to local and systemic aberrations in calcium and phosphorus metabolism. In addition, these surges in blood 25-hydroxyvitamin D levels promoted catabolism of both Vitamin D and 25-hydroxyvitamin D by 24-and/or 26-hydroxylation in the kidney and other tissues, down-regulation of hepatic production of Vitamin D prohormones, unnecessarily impeding the efficient repletion of Vitamin D insufficiency or deficiency, and, additional local aberrations in calcium and phosphorus homeostasis mediated by direct binding to VDR. Importantly, immediate release 25-hydroxyvitamin $D_3$ promoted its intestinal absorption via a mechanism substantially involving transport to the liver in chylomicrons, rather than bound to the serum DBP. Delivery of 25-hydroxyvitamin D to the liver via chylomicrons significantly increases the likelihood of its catabolism.

Clearly, a novel alternative approach to Vitamin D therapy is sorely needed, given the problems encountered with the currently available oral Vitamin D supplements and with previously used oral 25-hydroxyvitamin $D_3$. Given such an alternative approach, which is described herein, it becomes possible, for the first time, to concurrently apply Vitamin D repletion and Vitamin D hormone replacement therapies in CKD patients who have need of both types of therapies to effectively treat and subsequently prevent secondary hyperparathyroidism.

SUMMARY

In one aspect, the present invention provides a method of increasing or maintaining blood concentrations of both 25-hydroxyvitamin D and 1,25-dihydroxyvitamin D in a patient by administering, as necessary, both Vitamin D repletion and active Vitamin D hormone replacement therapies. The blood concentrations of 25-hydroxyvitamin D are increased to and maintained at or above 30 ng/mL, and blood concentrations of 1,25-dihydroxyvitamin D are increased to or maintained within a patient's normal historical physiological range for 1,25-dihydroxyvitamin D without causing substantially increased risk of hypercalcemia, hyperphosphatemia or over suppression of plasma iPTH in the patient. The blood levels of 25-hydroxyvitamin D are maintained at or above 30 ng/mL between doses of Vitamin D repletion therapies, and the blood levels of 1,25-dihydroxyvitamin D are maintained in the patient's normal historical physiological range between doses of Vitamin D hormone replacement therapies. In one preferred embodiment, the blood concentration of 25-hydroxyvitamin D during treatment comprises predominantly 25-hydroxyvitamin $D_3$, with a lesser amount of 25-hydroxyvitamin $D_2$. In another preferred embodiment, the method includes administering predominantly 25-hydroxyvitamin $D_3$, with a lesser amount of 25-hydroxyvitamin $D_2$, or solely 25-hydroxyvitamin $D_3$, for 25-hydroxyvitamin D repletion and/or maintenance.

In another aspect, the invention provides a method of concurrently lowering or maintaining plasma iPTH levels, increasing or maintaining serum calcium levels, maintaining serum phosphorous levels, increasing or maintaining serum 25-hydroxyvitamin D, and increasing or maintaining serum 1,25-dihydroxyvitamin D levels in a human patient by administering to the patient, as necessary, both Vitamin D repletion and Vitamin D hormone replacement therapies. The method can further include administration, as necessary, of phosphate binders and/or calcimimetic agents. In one preferred embodiment, the blood concentration of 25-hydroxyvitamin D during treatment comprises predominantly 25-hydroxyvitamin $D_3$, with a lesser amount of 25-hydroxyvitamin $D_2$. In another preferred embodiment, the method includes administering predominantly 25-hydroxyvitamin $D_3$, with a lesser amount of 25-hydroxyvitamin $D_2$, or solely 25-hydroxyvitamin $D_3$, for 25-hydroxyvitamin D repletion and/or maintenance.

In yet another aspect, the invention provides a method of reducing the risk of over suppression of plasma iPTH levels in a patient undergoing treatment for elevated levels of plasma iPTH, by administering, as necessary, both Vitamin D repletion and Vitamin D hormone replacement therapies in amounts sufficient to decrease elevated plasma iPTH levels while avoiding an abnormally low bone turnover rate. In one preferred embodiment, the blood concentration of 25-hydroxyvitamin D during treatment comprises predominantly 25-hydroxyvitamin $D_3$, with a lesser amount of 25-hydroxyvitamin $D_2$. In another preferred embodiment, the method includes administering predominantly 25-hydroxyvitamin $D_3$, with a lesser amount of 25-hydroxyvitamin $D_2$, or solely 25-hydroxyvitamin $D_3$, for 25-hydroxyvitamin D repletion and/or maintenance.

Another aspect of the invention is the use of at least one 25-hydroxyvitamin D and at least one active Vitamin D hormone for the preparation of a medicament for the treatment of a condition described herein, such as secondary hyperparathyroidism. In one preferred embodiment of such a use, the 25-hydroxyvitamin D comprises predominantly 25-hydroxyvitamin $D_3$, with a lesser amount of 25-hydroxyvitamin $D_2$.

Another aspect of the invention is a kit for treatment of a condition described herein, such as secondary hyperparathyroidism, including a 25-hydroxyvitamin D compound, or an active Vitamin D hormone, or combinations thereof, and written instructions for co-treatment with a 25-hydroxyvitamin D compound and an active Vitamin D hormone.

Optionally excluded from the methods of the invention are therapeutic treatment of subjects suffering from renal osteodystrophy (including osteomalacia and osteitis fibrosa cystica).

A fuller appreciation of the specific attributes of this invention will be gained upon an examination of the following detailed description of preferred embodiments, and the appended claim. Before the embodiments of the invention are explained in detail, it is to be understood that the invention is not limited in its application to the details of construction and the arrangements of the components set forth in the following description. The invention is capable of other embodiments and of being practiced or being carried out in various ways. Also, it is understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

DETAILED DESCRIPTION

The present invention relates to treating and preventing secondary hyperparathyroidism and the underlying chronically low blood levels of 1,25-dihydroxyvitamin D, and various other related abnormalities in mineral and bone metabolism, by administering effective amounts, as necessary, of both Vitamin D repletion and Vitamin D hormone replacement therapies.

In one aspect the present invention provides a method of increasing and then maintaining blood concentrations of 25-hydroxyvitamin D at or above 30 ng/mL, and blood concentrations of 1,25-dihydroxyvitamin D to within a patient's normal historical physiological range for 1,25-dihydroxyvitamin D. As noted hereinbefore, many conditions can lead to chronically low blood levels of 1,25-dihydroxyvitamin D, including CKD (e.g., Stages 3 and 4, and Stage 5), living in northern latitudes and insufficient intake of cholecalciferol and/or ergocalciferol. It has been found that treatment, as needed, with both Vitamin D repletion and Vitamin D hormone replacement therapies of those patients in need thereof can provide blood concentrations of 25-hydroxyvitamin D at or above 30 ng/mL and blood concentrations of 1,25-dihydroxyvitamin D within the patient's normal historical physiological range. One or both of the Vitamin D repletion and Vitamin D hormone replacement therapies, and preferably both, are preferably administered in a manner to avoid bolus surges of Vitamin D in the intestinal lumen or in the blood, thereby avoiding substantially increased risk of hypercalcemia, hyperphosphatemia or over suppression of plasma iPTH in the patient, all of which have been recognized as risks when treatment with a vitamin D therapy is undertaken. Moreover, blood levels of 25-hydroxyvitamin D are maintained above 30 ng/mL and blood levels of 1,25-dihydroxyvitamin D are maintained in the patient's historical physiological range between therapeutic doses. In one preferred embodiment, the blood concentration of 25-hydroxyvitamin D comprises predominantly 25-hydroxyvitamin $D_3$. In another preferred embodiment, the method includes administering predominantly or solely 25-hydroxyvitamin $D_3$ for 25-hydroxyvitamin D repletion and/or maintenance.

In another aspect, the invention provides a method of concurrently lowering or maintaining plasma iPTH levels, increasing or maintaining serum calcium levels, maintaining serum phosphorous levels, increasing or maintaining serum 25-hydroxyvitamin D levels, and increasing or maintaining serum 1,25-dihydroxyvitamin D levels in a human patient by administering to the patient, as needed, effective amounts of both Vitamin D repletion and Vitamin D hormone replacement therapies. Many diseases manifest abnormal levels of more than one hormone and mineral. In CKD, for example, patients may experience decreases in serum total 1,25-dihydroxyvitamin D, increases in plasma iPTH, decreases in serum calcium and increases in serum phosphorous. Treatment in accordance with the present invention presents concurrent leveling and/or maintaining of these various hormone and mineral levels. In one preferred embodiment, the blood concentration of 25-hydroxyvitamin D comprises predominantly 25-hydroxyvitamin $D_3$. In another preferred embodiment, the method includes administering predominantly or solely 25-hydroxyvitamin $D_3$ for 25-hydroxyvitamin D repletion and/or maintenance. Treatment of patients having Stage 3 or 4 CKD, or Stage 5 CKD, is particularly contemplated.

The subject's PTH levels preferably are lowered by at least 30%, or alternatively to the target range for the CKD stage (e.g., for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1)).

Another aspect of the invention is a kit for treatment of a condition described herein, such as Vitamin D deficiency or secondary hyperparathyroidism, including a 25-hydroxyvitamin D compound, or an active Vitamin D hormone, or combinations thereof, and written instructions for co-treatment with a 25-hydroxyvitamin D compound and an active Vitamin D hormone. For example, the kit can include a 25-hydroxyvitamin D compound, such as 25-hydroxyvitamin $D_3$, and written instructions for co-treatment of a subject with the 25-hydroxyvitamin D compound and an active Vitamin D hormone, such as 1,25-dihydroxyvitamin $D_2$. As another example, the kit can include an active Vitamin D hormone and written instructions for co-treatment of a subject with the active Vitamin D hormone and a 25-hydroxyvitamin D compound. As still another example, the kit can include both a 25-hydroxyvitamin D compound and an active Vitamin D hormone, and written instructions for co-treatment of a subject with the 25-hydroxyvitamin D compound and the active Vitamin D hormone. Co-treatment can be according to the disclosure hereinbelow, and can include co-administration and administration at different discrete intervals but overlapping in a term of periodic administration of the compounds. Co-administration includes concurrent administration, and is not limited to simultaneous administration. Co-treatment can include administration by the same or different routes of administration.

"Co-administration" means the administration of two or more compounds to the same patient. For example, co-administration encompasses (a) simultaneous administration of a first and second compound and (b) administration of a first compound, followed by administration of a second compound. For example, the first and second compounds can be administered within 24 hours, 8 hours, 4 hours, 2 hours, or 1 hour of each other. In other embodiments, different time periods of between administration of first and second compounds may be applicable.

"Supraphysiologic" in reference to intraluminal, intracellular and blood levels of Vitamin D refers to a total concentration of the vitamin D compound markedly greater than the generally stable levels observed in a Vitamin D-replete subject, animal or human patient over the course of any 24-hour period by laboratory measurement when Vitamin D supplementation has been withheld for at least 30 days. "Adverse supraphysiologic surge" refers to a local or serum concentration of a vitamin D compound that elicits adverse effects such as excessive extrarenal hormone production, leading to local adverse effects on calcium and phosphorus metabolism, inhibition of hepatic 25-hydroxylation of vitamin D, increased catabolism of both Vitamin D and 25-hydroxyvitamin D, hypercalciuria, hypercalcemia and/or hyperphosphatemia, with possible cardiovascular sequelae.

As used herein, the term "patient's normal historical physiological range of serum 1,25-dihydroxyvitamin D" refers to the average blood concentration range of 1,25-dihydroxyvitamin D of a patient based on at least two annual or biannual readings of serum 1,25-dihydroxyvitamin D levels taken while the kidneys are healthy.

As used herein the term "hypercalcemia" refers to condition in a patient wherein the patient has corrected serum levels of calcium above 10.2 mg/dL. Normal corrected serum levels of calcium for a human are between about 8.6 to 10.2 mg/dL.

As used herein, the term "hyperparathyroidism" refers to primary hyperparathyroidism, secondary hyperparathyroidism and hyperparathyroidism secondary to chronic kidney disease (Stage 3, 4 or 5).

The term "subject" as used herein generally includes humans, mammals (e.g., dogs, cats, rodents, sheep, horses, cows, goats), veterinary animals and zoo animals.

As used herein the term "hyperphosphatemia" refers to a condition in a patient having normal kidney function, or Stage 1-4 CKD, wherein the patient has serum phosphorous levels above 4.6 mg/dL. In a patient who has Stage 5 CKD, hyperphosphatemia occurs when the patient has serum levels above 5.5 mg/dL. Normal values for serum phosphorous in a human are 2.4-4.5 mg/dL.

As used herein the term "over suppression of plasma iPTH" refers to a condition in a patient having normal kidney function, or Stage 1-3 CKD, wherein the patient has levels of plasma iPTH below 15 pg/mL. In a patient having Stage 4 CKD, over suppression of plasma iPTH occurs when the patient has levels of plasma iPTH below 30 pg/mL. In a patient having Stage 5 CKD, over suppression of plasma iPTH occurs when the patient has levels of plasma iPTH below 100 pg/mL.

As used herein, the term "abnormally low bone turnover rate" refers to a condition in a patient wherein the rate of bone resorption is greater than the rate of bone formation.

As used herein, the term "Vitamin D repletion therapy" refers to the administration to a patient of an effective amount of a Vitamin D, a Vitamin D analog, a Vitamin D prohormone, and a Vitamin D prohormone analog. Particularly preferred are ergocalciferol, cholecalciferol, 25-hydroxyvitamin $D_2$, and 25-hydroxyvitamin $D_3$. The Vitamin D repletion therapy can be via any route of administration. In one preferred embodiment, the therapy will result in blood concentration of 25-hydroxyvitamin D comprising predominantly 25-hydroxyvitamin $D_3$. For example, in any of the methods described herein, the blood concentration of 25-hydroxyvitamin D will comprise greater than 50% 25-hydroxyvitamin $D_3$, or at least 60%, at least 70%, at least 80%, or at least 90% 25-hydroxyvitamin $D_3$. In another preferred embodiment, the therapy includes administering predominantly or solely 25-hydroxyvitamin $D_3$ for 25-hydroxyvitamin D repletion and/or maintenance. For example, in any of the methods described herein, the administration of 25-hydroxyvitamin D will comprise greater than 50% 25-hydroxyvitamin $D_3$, or at least 60%, at least 70%, at least 80%, at least 90%, or solely 25-hydroxyvitamin $D_3$.

As used herein, the term "Vitamin D hormone replacement therapy" refers to the administration to a patient of an effective amount of one or more of active vitamin D hormones, which include an active Vitamin D hormone metabolites, and active Vitamin D hormone analogs, such as 1α-hydroxylated Vitamin D compounds. Metabolites and analogs of Vitamin D which can substantially occupy the intracellular VDR or activate the VDR are preferred. 1,25-dihydroxyvitamin $D_2$, 1,25-dihydroxyvitamin $D_3$, 1,25-dihydroxyvitamin $D_4$, and analogs thereof are preferred.

As used herein, the term "controlled release" and "sustained release" are used interchangeably, and refer to the release of the administered vitamin D compound in a way that deviates from immediate release. The term "controlled release" optionally includes delayed release characteristics. For example, a delayed release type of controlled release formulation will be characterized by Cmax at a time greater than Cmax for an immediate release formulation. As another example, the release of an administered Vitamin D compound will preferably be at such a rate that total serum or blood levels of the Vitamin D compound are maintained or elevated above predosing levels for an extended period of time, e.g. 25-hydroxyvitamin D elevated for 4 to 24 hours or even longer. As another example, a sustained release type of controlled release formulation will be characterized by release at such a rate that total serum or blood levels of an active Vitamin D hormone are maintained or elevated above predosing levels for an extended period of time, e.g. 20 to 40 minutes, 1 to 15 hours or even longer.

In a method including controlled release of a Vitamin D compound (i.e. one or both of the compound(s) for Vitamin D repletion and active Vitamin D hormone replacement), the release rate of the vitamin D compound is controlled to reduce Cmax and/or delay Tmax and/or decrease $Cmax_{24hr}/C_{24hr}$, as described herein. Preferably both Cmax is reduced and Tmax is delayed (increased).

Thus, one embodiment includes a method of administering an amount of a vitamin D compound to a subject such that the maximum serum concentration of the vitamin D compound in a dose interval (Cmax) is reduced as compared to Cmax for an equivalent amount of a vitamin D compound administered by bolus IV injection and/or an equivalent immediate-release, oral dosage form. For example, the reduction is preferably by a factor of at least 50%, 60%, 70%, or 80%.

Another embodiment includes a method of administering an amount of a vitamin D compound to a subject such that the maximum change in serum concentration of a vitamin D compound in a dose interval is reduced as compared to an equivalent amount of a vitamin D compound administered by bolus IV injection and/or an equivalent immediate-release, oral dosage form. For example, the reduction is preferably by a factor of at least 50%, 60%, 70%, or 80%.

Still another embodiment includes a method of administering an amount of a vitamin D compound to a patient such that the ratio of the maximum serum concentration within 24 hours after administration of a vitamin D compound to the concentration 24 hours after administration ($Cmax_{24hr}/C_{24hr}$) is reduced as compared to an equivalent amount of a vitamin D compound administered by bolus IV injection and/or an equivalent immediate-release, oral dosage form. For example, the reduction is preferably by a factor of at least 50%, 60%, 70%, or 80%.

Yet another embodiment includes a method of administering an amount of a vitamin D compound to a subject such that the elimination half-life ($t_{1/2}$) of a vitamin D compound is increased as compared to $t_{1/2}$ for an equivalent amount of a vitamin D compound administered by bolus IV injection and/or an equivalent immediate-release, oral dosage form. For example, the increase is preferably by a factor of at least 25%, 30%, 40%, 50%, or 60%.

A further embodiment includes a method of administering an amount of a vitamin D compound to a subject such that the time for the plasma concentration of a vitamin D compound to reach its maximum in a dose interval following administration (Tmax) is increased as compared to Tmax for an equivalent amount of a vitamin D compound administered by bolus IV injection and/or an equivalent immediate-release, oral dosage form. For example, the increase is preferably by a factor of at least 25%, 30%, 40%, 50%, or 60%.

Furthermore, the compositions optionally can be designed for delayed release into the ileum of the gastrointestinal tract of humans or animals. It is contemplated that in one type of embodiment the compositions will ensure a substantially constant concentration of the desired Vitamin D compound in the body, and a more sustained blood level. By providing a slow and steady release over time, blood, intraluminal and intracellular concentration spikes, e.g., adverse supraphysiologic levels, are mitigated or eliminated.

Ergocalciferol, cholecalciferol, 25-hydroxyvitamin $D_2$ and/or 25-hydroxyvitamin $D_2$ 1,25-dihydroxyvitamin $D_3$, 1,25-dihydroxyvitamin $D_2$, 1,25-dihydroxyvitamin $D_4$, and other metabolites and analogs of Vitamin D are also useful as active compounds in pharmaceutical compositions. The pharmacologically active analogs of this invention can be processed in accordance with conventional methods of pharmacy to produce pharmaceutical agents for administration to patients, e.g., in admixtures with conventional excipients such as pharmaceutically acceptable organic or inorganic carrier substances suitable for parenteral, enteral (e.g., oral), topical or transdermal application which do not deleteriously react with the active compounds. Suitable pharmaceutically acceptable carriers include, but are not limited to, water, salt (buffer) solutions, alcohols, gum arabic, mineral and vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic active compounds. If a pharmaceutically acceptable solid carrier is used, the dosage form of the analogs may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragées, liquids, drops, suppositories, or capsules such as soft gelatin capsules. A syrup, elixir, or the like can be used wherein a sweetened vehicle is employed.

Controlled release compositions can be formulated, e.g., liposomes or those wherein the active compound is protected with differentially degradable coatings, such as by microencapsulation, multiple coatings, etc. It is also possible to freeze-dry the new compounds and use the lyophilizates obtained, for example, for the preparation of products for injection. Transdermal delivery of pharmaceutical compositions of the compounds of the invention is also possible.

For topical application, there are employed as nonsprayable forms, viscous to semi-solid or solid forms comprising a carrier compatible with topical application and having a dynamic viscosity preferably greater than water. Suitable formulations include, but are not limited to, solutions, suspensions, emulsions, creams, ointments, powders, liniments, salves, aerosols, etc., which are, if desired, sterilized or mixed with auxiliary agents, e.g., preservatives, etc.

It is possible, if desired, to produce the metabolites of certain ones of the compounds of the invention, in particular by nonchemical means. For this purpose, it is possible to convert them into a suitable form for administration together with at least one vehicle or auxiliary and, where appropriate, combined with one or more other active compounds.

The dosage forms may also contain adjuvants, such as preserving or stabilizing adjuvants. They may also contain other therapeutically valuable substances or may contain more than one of the compounds specified herein and in the claims in admixture.

As described hereinbefore, Vitamin D repletion and Vitamin D hormone replacement therapies are preferably administered to the human patients in oral or intravenous dosage formulations. The administration of such therapies, in accordance with the present invention, can be on an episodic basis, suitably from daily, to 1 to 3 times a week. Suitably the dosage of Vitamin D repletion therapy or Vitamin D hormone replacement therapy is about 0.5 μg to about 400 μg per week, depending on the agent selected. Suitably such therapies can be given in a unit dosage form between about 0.5 μg to about 100 μg, or about 0.5 μg to about 10 μg in a pharmaceutically acceptable carrier per unit dosage. Episodic doses can be a single dose or, optionally, divided into 2-4 subdoses which, if desired, can be given, e.g., twenty minutes to an hour apart until the total dose is given.

The dosage of a 1,25-dihydroxyvitamin D for oral administration generally is about 0.1 μg per week to 100 μg per week, preferably about 0.7 μg per week to about 70 μg per week, which can be split into daily or other periodic doses, such as three times per week for administration concomitant with hemodialysis. In exemplary embodiments, an oral dosage equivalent to about 1, 2, 3, 4, 5, 6, 7, 8 or 9 μg per day is contemplated.

Generally, a 1,25-dihydroxyvitamin D compound can be dispensed by unit dosage form comprising about 0.1 μg to about 10 μg per unit dosage, for example about 1 μg to about 4 μg, about 2 μg to about 10 μg, or about 3 μg to about 5 μg.

The duration of the treatment is contemplated to be at least four weeks, or at least twelve weeks, and can be ongoing for years or even decades.

A controlled release composition intended for oral administration for Vitamin D repletion in accordance with the methods described herein preferably is designed to contain concentrations of the 25-hydroxyvitamin $D_3$, for example, of 1 to 100 μg per unit dose and are prepared in such a manner as to effect controlled or substantially constant release of the 25-hydroxyvitamin D, optionally into the ileum of the gastrointestinal tract, of humans or animals over an extended period of time. The compositions and methods may provide substantially increased absorption of 25-hydroxyvitamin D via transport on DBP and decreased absorption via transport in chylomicrons. The compositions and methods may provide maintenance of substantially constant blood levels of 25-hydroxyvitamin D during the 24-hour post-dosing period. By providing both a gradual, sustained and direct release of the 25-hydroxyvitamin D and absorption preferentially to circulating DBP (rather than to chylomicrons), blood, intraluminal and intracellular 25-hydroxyvitamin D concentration spikes, i.e., supraphysiologic levels and related unwanted catabolism can be mitigated or eliminated.

Advantageously, the compound, such as 25-hydroxyvitamin $D_3$, together with other therapeutic agents can be orally or intravenously administered in accordance with the above described embodiments in dosage amounts of from 1 to 100 μg per day, with the preferred dosage amounts of from 5 to 50 μg per day, for example about 10 to 25 μg. Preferred doses will provide an average rise in serum 25-hydroxyvitamin $D_3$ of about 1 to 3 ng/mL.

In embodiments, the method is contemplated to include administering a formulation described herein to raise and preferably also maintain blood 1,25-dihydroxyvitamin D levels at 25 pg/mL, 30 pg/mL, or higher, e.g. 25-65 pg/mL for an extended period, for example at least one month, at least three months, at least six months, or longer.

Those of ordinary skill in the art will readily optimize effective doses and co-administration regimens as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, sex, body weight, general state of health, on diet, on the timing and mode of administration, on the rate of excretion, and on medicaments used in combination and the severity of the particular disorder to which the therapy is applied. Dosages for a given patient can be determined using conventional considerations, e.g., by customary comparison of the differential activities of the subject compounds and of a known agent, such as by means of an appropriate conventional pharmacological protocol. A physician of ordinary skill can readily determine and prescribe the effective amount of the drug required to counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. The dosage of active ingredient in the compositions of this invention may be varied; however, it is necessary that the amount of the active ingredient be such that an efficacious dosage is obtained. The active ingredient is administered to patients (animal and human) in need of treatment in dosages that will provide optimal pharmaceutical efficacy.

Bulk quantities of Vitamin D and Vitamin D analogs in accordance with the present invention can be readily obtained in accordance with the many widely known processes.

The present invention is further explained by the following examples which should not be construed by way of limiting the scope of the present invention. The following examples demonstrate that the concomitant administration of Vitamin D repletion and Vitamin D hormone replacement therapies has improved efficacy in reducing or preventing elevated blood PTH levels as well as maintaining adequate and appropriate levels of serum calcium, serum phosphorous, serum total 25-hydroxyvitamin D and serum total 1,25-dihydroxyvitamin D.

EXAMPLES

The following examples are provided for illustration and are not intended to limit the scope of the invention.

Example 1

Efficacy Study in Adult Patients With CKD and Secondary Hyperparathyroidism

The effectiveness of three different Vitamin D treatment regimens in controlling elevated serum iPTH is examined in a 26-week study of non-obese patients diagnosed with secondary hyperparathyroidism and CKD. Two formulations containing Vitamin D are prepared. One of the formulations (Formulation #1) is a soft gelatin capsule containing 5,000 IU of Vitamin D, comprised of a mixture of 2,500 IU of cholecalciferol and 2,500 IU of ergocalciferol and prepared in a delayed sustained release formulation. The second formulation (Formulation #2) is soft gelatin capsule of identical appearance containing 0.5 mcg of 1,25-dihydroxyvitamin $D_2$ prepared in a delayed sustained release formulation. A total of 100 Caucasian and African-American patients participate in this study, all of whom are aged 30 to 70 years, have Stage 4 CKD, exhibit serum calcium levels between 8.6 and 10.2 mg/dL (inclusive), exhibit serum phosphorus levels below 4.5 mg/dL, have serum total 25-hydroxyvitamin D levels between 5 and 15 ng/mL (inclusive), have serum total 1,25-dihydroxyvitamin D between 5 and 15 pg/mL (inclusive), and have plasma iPTH above 250 pg/mL. All subjects abstain from taking Vitamin D therapies of any kind for 60 days before study start and, except for the test formulations, continuing through study termination. On Day 1 and 2 of the study, all subjects provide fasting morning blood samples to establish pre-treatment baseline values of serum total 25-hydroxyvitamin D, serum total 1,25-dihydroxyvitamin D, plasma iPTH, serum calcium and serum phosphorus. On the morning of Day 3, the subjects provide an additional fasting blood sample (t=0), are randomly assigned to one of four treatment groups, and are dosed daily for 26 weeks prior to eating breakfast: the subjects in Group #1 each receive a single capsule of Formulation #1; the subjects in Group #2 each receive a single capsule of Formulation #2; the subjects in Group #3 each receive a single capsule of Formulation #1 plus a single capsule of Formulation #2; and, subjects in Group #4 receive a matching placebo capsule. A fasting morning blood sample is drawn from each subject, irrespective of treatment group, at weekly intervals just prior to dosing. All collected blood is analyzed for the contained levels of 25-hydroxyvitamin D, 1,25-dihydroxyvitamin D, plasma iPTH, serum calcium and serum phosphorus, and the data are analyzed by treatment group. Subjects in all four treatment groups exhibit mean baseline serum total 25-hydroxyvitamin D levels of approximately 8-11 ng/mL, based on analysis of fasting blood samples drawn on Days 1 through 3. Subjects in Group #4 (control group) show no significant changes in any of the parameters measured over the course of the study. Subjects in Group #1 show during treatment a steadily increasing mean serum 25-hydroxyvitamin D reaching approximately 34 ng/mL, a significant reduction in plasma iPTH, and no significant changes in the other measured parameters. Subjects in Group #2 show a significant increase in serum total 1,25-dihydroxyvitamin D, a significant decrease in iPTH, slightly increasing trends in serum calcium and serum phosphorus, and no significant changes in mean serum 25-hydroxyvitamin D. Subjects in Group #3 exhibit the same changes observed in Group #2 except that (a) the decrease in iPTH over the course of the treatment period is significantly greater by study end than in Groups #1 and #2, and (b) serum total 25-hydroxyvitamin D show steadily increasing mean serum 25-hydroxyvitamin D reaching approximately 36 ng/mL by Week 26. The data from this study demonstrate that administration of both Vitamin D repletion therapy and Vitamin D hormone replacement therapy is substantially more effective in controlling secondary hyperparathyroidism and normalizing serum total levels of both 25-hydroxyvitamin D and 1,25-dihydroxyvitamin D without causing unwanted aberrations in serum calcium and serum phosphorus in patients with CKD Stage 4.

Example 2

Efficacy Study in Adult Patients With CKD and Secondary Hyperparathyroidism

The effectiveness of three different Vitamin D treatment regimens in controlling elevated serum iPTH is examined in a 26-week study of non-obese patients diagnosed with secondary hyperparathyroidism and CKD. Two formulations containing Vitamin D are prepared. One of the formulations (Formulation #1) is a soft gelatin capsule containing 5,000 IU of Vitamin D, comprised of a mixture of 4,000 IU of cholecalciferol and 1,000 IU of ergocalciferol and prepared in a delayed sustained release formulation. The second formulation (Formulation #2) is soft gelatin capsule of identical appearance containing 0.5 mcg of 1,25-dihydroxyvitamin $D_2$ prepared in a delayed sustained release formulation. A total of 100 Caucasian and African-American patients participate in this study, all of whom are aged 30 to 70 years, have Stage 4 CKD, exhibit serum calcium levels between 8.6 and 10.2 mg/dL (inclusive), exhibit serum phosphorus levels below 4.5 mg/dL, have serum total 25-hydroxyvitamin D levels between 5 and 15 ng/mL (inclusive), have serum total 1,25-dihydroxyvitamin D between 5 and 15 pg/mL (inclusive), and have plasma iPTH above 250 pg/mL. All subjects abstain from taking Vitamin D therapies of any kind for 60 days before study start and, except for the test formulations, continuing through study termination. On Day 1 and 2 of the study, all subjects provide fasting morning blood samples to establish pre-treatment baseline values of serum total 25-hydroxyvitamin D, serum total 1,25-dihydroxyvitamin D, plasma iPTH, serum calcium and serum phosphorus. On the morning of Day 3, the subjects provide an additional fasting blood sample (t=0), are randomly assigned to one of four treatment groups, and are dosed daily for 26 weeks prior to eating breakfast: the subjects in Group #1 each receive a single capsule of Formulation #1; the subjects in Group #2 each receive a single capsule of Formulation #2; the subjects in Group #3 each receive a single capsule of Formulation #1 plus a single capsule of Formulation #2; and, subjects in Group #4 receive a matching placebo capsule. A fasting morning blood sample is drawn from each subject, irrespective of treatment group, at weekly intervals just prior to dosing. All collected blood is analyzed for the contained levels of 25-hydroxyvitamin D, 1,25-dihydroxyvitamin D, plasma iPTH, serum calcium and serum phosphorus, and the data are analyzed by treatment group. Subjects in all four treatment groups exhibit mean baseline serum total 25-hydroxyvitamin D levels of approximately 8-11 ng/mL, based on analysis of fasting blood samples drawn on Days 1 through 3. Subjects in Group #4 (control group) show no significant changes in any of the parameters measured over the course of the study. Subjects in Group #1 show during treatment a significant increase in mean serum 25-hydroxyvitamin D (with the predominant species being 25-hydroxyvitamin $D_3$), a significant reduction in plasma iPTH, and no significant changes in the other measured parameters. Subjects in Group #2 show a significant increase in serum total 1,25-dihydroxyvitamin D, a significant decrease in iPTH, slightly increasing trends in serum calcium and serum phosphorus, and no significant changes in mean serum 25-hydroxyvitamin D. Subjects in Group #3 exhibit the same changes observed in Group #2 except that (a) the decrease in iPTH over the course of the treatment period is significantly greater by study end than in Groups #1 and #2, and (b) serum total 25-hydroxyvitamin D show significantly increased mean serum 25-hydroxyvitamin D by Week 26. The data from this study demonstrate that administration of both Vitamin D repletion therapy and Vitamin D hormone replacement therapy is substantially more effective in controlling secondary hyperparathyroidism and normalizing serum total levels of both 25-hydroxyvitamin D and 1,25-dihydroxyvitamin D without causing unwanted aberrations in serum calcium and serum phosphorus in patients with CKD Stage 4.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

All patents, publications and references cited herein are hereby fully incorporated by reference. In case of conflict between the present disclosure and incorporated patents, publications and references, the present disclosure should control.

Embodiments contemplated in view of the foregoing description include the following numbered paragraphs.

1. A method of increasing or maintaining blood concentrations of both 25-hydroxyvitamin D and 1,25-dihydroxyvitamin D in a human patient, including administering both Vitamin D repletion and Vitamin D hormone replacement therapies, wherein the blood concentrations of 25-hydroxyvitamin D are increased to and maintained at or above 30 ng/mL, and blood concentrations of 1,25-dihydroxyvitamin D are increased to or maintained within a patient's normal historical physiological range for 1,25-dihydroxyvitamin D.

2. A method of concurrently lowering or maintaining plasma iPTH levels, increasing or maintaining serum calcium levels, maintaining serum phosphorous levels, increasing or maintaining serum 25-hydroxyvitamin D, and increasing or maintaining serum 1,25-dihydroxyvitamin D levels in a human patient by administering to the patient both Vitamin D repletion and Vitamin D hormone replacement therapies.

3. A method of reducing the risk of over suppression of plasma iPTH levels in a patient undergoing treatment for elevated levels of plasma iPTH, including administering both Vitamin D repletion and Vitamin D hormone replacement therapies in amounts sufficient to decrease elevated plasma iPTH levels while avoiding an abnormally low bone turnover rate.

4. A method of maintaining in a patient blood concentrations of 25-hydroxyvitamin D at or above 30 ng/mL and blood concentrations of 1,25-dihydroxyvitamin D in a patient at levels within the patient's normal historical physiological range while lowering elevated blood levels if iPTH without causing substantially increased risk of hypercalcemia, hyperphosphatemia or over suppression of plasma iPTH including administering to the patient an effective amount, as needed, of both a Vitamin D repletion therapy and a Vitamin D hormone replacement therapy.

5. The method according to any one of the preceding paragraphs, wherein the blood levels of 25-hydroxyvitamin D are maintained at or above 30 ng/mL between doses of Vitamin D repletion therapies, and the blood levels of 1,25-dihydroxyvitamin D are maintained in the patient's normal historical physiological range between doses of Vitamin D hormone replacement therapies.

6. The method according to any one of the preceding paragraphs, wherein the blood concentration of 25-hydroxyvitamin D during treatment includes predominantly 25-hydroxyvitamin $D_3$.

7. The method according to any one of the preceding paragraphs, wherein the administering of Vitamin D repletion includes administering predominantly 25-hydroxyvitamin $D_3$.

8. The method according to any one of the preceding paragraphs, wherein the administering of Vitamin D repletion therapy includes controllably releasing a compound for Vitamin D repletion.

9. The method according to any one of the preceding paragraphs, wherein the administering of Vitamin D hormone replacement therapy includes controllably releasing a compound for Vitamin D hormone replacement.

10. The method according to any one of the preceding paragraphs, wherein the patient suffers from chronic kidney disease.

11. The method of paragraph 10, wherein the chronic kidney disease is Stage 1, Stage 2, Stage 3, or Stage 4.

12. The method of paragraph 10, wherein the chronic kidney disease is Stage 3, Stage 4, or Stage 5.

13. The method of paragraph 12, wherein the chronic kidney disease is Stage 3 or Stage 4.

14. The method of paragraph 12, wherein the chronic kidney disease is Stage 5.

15. The method according to any one of the preceding paragraphs, further including co-treatment with a phosphate binder.

16. The method according to any one of the preceding paragraphs, further including co-treatment with a calcimimetic agent.

17. The method according to paragraph 2, wherein the administering of Vitamin D repletion comprises administering predominantly 25-hydroxyvitamin $D_3$.

18. The method according to paragraph 3, wherein the administering of Vitamin D repletion comprises administering predominantly 25-hydroxyvitamin $D_3$.

19. The method according to paragraph 4, wherein the administering of Vitamin D repletion comprises administering predominantly 25-hydroxyvitamin $D_3$.

20. The method according to paragraph 2, wherein the patient suffers from chronic kidney disease.

What is claimed is:

1. A method of treating or preventing secondary hyperparathyroidism in Chronic Kidney Disease (CKD) Stage 3 or Stage 4 in a human patient, comprising administering to the patient both Vitamin D repletion and Vitamin D hormone replacement therapies.

2. The method of claim 1, wherein the Vitamin D repletion therapy comprises administering to the patient a compound for Vitamin D repletion selected from the group consisting of ergocalciferol, cholecalciferol, 25-hydroxyvitamin $D_3$, 25-hydroxyvitamin $D_2$, and combinations thereof.

3. The method of claim 2, wherein the repletion therapy comprises administering to the patient a combination of 25-hydroxyvitamin $D_2$ and 25-hydroxyvitamin $D_3$.

4. The method of claim 2, wherein the compound for Vitamin D repletion is 25-hydroxyvitamin $D_3$.

5. The method of claim 2, wherein the repletion therapy comprises administering to the patient a combination of ergocalciferol and cholecalciferol.

6. The method of claim 1, wherein the Vitamin D hormone replacement therapy comprises administering to the patient a compound for Vitamin D hormone replacement selected from the group consisting of 1,25-dihydroxyvitamin $D_2$, 1,25-dihydroxyvitamin $D_3$, 1,25-dihydroxyvitamin $D_4$, 1α-hydroxyvitamin $D_2$, 1αhydroxyvitamin $D_3$, and combinations thereof.

7. The method of claim 6, wherein the compound for Vitamin D hormone replacement is 1,25-dihydroxyvitamin $D_2$.

8. The method of claim 1, wherein the Vitamin D repletion therapy and/or the Vitamin D hormone replacement therapy comprises controllably releasing a compound for Vitamin D repletion and/or Vitamin D hormone replacement.

9. The method of claim 8, wherein the Vitamin D repletion therapy comprises controllably releasing a compound for Vitamin D repletion.

10. The method of claim 8, wherein the Vitamin D hormone replacement therapy comprises controllably releasing a compound for Vitamin D hormone replacement.

11. The method of claim 8, wherein controllably releasing a compound comprises reducing the maximum serum concentration of the compound in a dose interval (Cmax) compared to an equivalent amount of the compound administered by bolus IV injection and/or an equivalent immediate-release, oral dosage form.

12. The method of claim 8, wherein controllably releasing a compound comprises increasing the time for the plasma concentration of the compound to reach its maximum in a dose interval following administration (Tmax) compared to an equivalent amount of the compound administered by bolus IV injection and/or an equivalent immediate-release, oral dosage form.

13. The method of claim 8, wherein controllably releasing a compound comprises decreasing the ratio of the maximum serum concentration within 24 hours after administration of the compound to the concentration 24 hours after administration ($Cmax_{24hr}/C_{24hr}$) compared to an equivalent amount of the compound administered by bolus IV injection and/or an immediate-release, oral dosage form.

14. The method of claim 1, comprising administering to the patient both Vitamin D repletion and Vitamin D hormone replacement therapies to lower the patient's serum parathyroid level by at least 30%.

15. The method of claim 1, comprising administering to the patient both Vitamin D repletion and Vitamin D hormone replacement therapies to lower the patient's serum parathyroid level to the target range for the CKD stage.

16. The method of claim 1, comprising administering to the patient both Vitamin D repletion and Vitamin D hormone replacement therapies such that oversuppression of the patient's serum parathyroid hormone is avoided.

17. The method of claim 1, where the patient does not have renal osteodystrophy.

18. The method of claim 1, comprising administering to the patient both Vitamin D repletion and Vitamin D hormone replacement therapies to increase or maintain the patient's blood level of 25-hydroxyvitamin D to at least 30 ng/mL.

19. The method of claim 1, comprising administering to the patient both Vitamin D repletion and Vitamin D hormone replacement therapies to increase or maintain the patient's blood level of 1,25-dihydroxyvitamin D to at least 25 pg/mL.

20. The method of claim 1, comprising administering to the patient both Vitamin D repletion and Vitamin D hormone replacement therapies such that the patient's blood level of 25-hydroxyvitamin D comprises predominantly 25-hydroxyvitamin $D_3$.

21. The method of claim 1, comprising administering to the patient both Vitamin D repletion and Vitamin D hormone replacement therapies to avoid supraphysiologic levels of 25-hydroxyvitamin D.

* * * * *